US012514707B2

(12) United States Patent
Cole et al.

(10) Patent No.: US 12,514,707 B2
(45) Date of Patent: Jan. 6, 2026

(54) MEDICAL DEVICES FOR SHUNTS, OCCLUDERS, FENESTRATIONS AND RELATED SYSTEMS AND METHODS

(71) Applicant: W. L. Gore & Associates, Inc., Newark, DE (US)

(72) Inventors: Daniel S. Cole, Flagstaff, AZ (US); Tom R. McDaniel, Flagstaff, AZ (US); Edward E. Shaw, Flagstaff, AZ (US); Benjamin A. Smith, Flagstaff, AZ (US); Jerome Adam-Cote, San Francisco, CA (US); Ian R. Berve, Mountain, CA (US); Barrett S. Hutto, Santa Cruz, CA (US); James A. McCrea, San Carlos, CA (US)

(73) Assignee: W. L. Gore & Associates, Inc., Newark, DE (US)

( * ) Notice: Subject to any disclaimer, the term of this patent is extended or adjusted under 35 U.S.C. 154(b) by 558 days.

(21) Appl. No.: 17/793,504

(22) PCT Filed: Jan. 14, 2021

(86) PCT No.: PCT/US2021/013411

§ 371 (c)(1),
(2) Date: Jul. 18, 2022

(87) PCT Pub. No.: WO2021/146405

PCT Pub. Date: Jul. 22, 2021

(65) Prior Publication Data

US 2023/0074508 A1 Mar. 9, 2023

Related U.S. Application Data

(60) Provisional application No. 62/962,541, filed on Jan. 17, 2020.

(51) Int. Cl.
*A61F 2/24* (2006.01)

(52) U.S. Cl.
CPC .................................. *A61F 2/2487* (2013.01)

(58) Field of Classification Search
CPC ......... A61F 2/2487; A61B 2017/00022; A61B 2017/00243; A61B 17/11;
(Continued)

(56) References Cited

U.S. PATENT DOCUMENTS

| | | |
|---|---|---|
| 3,953,566 A | 4/1976 | Gore |
| 4,187,390 A | 2/1980 | Gore |

(Continued)

FOREIGN PATENT DOCUMENTS

| | | |
|---|---|---|
| CN | 1218414 A | 6/1999 |
| CN | 102438546 A | 5/2012 |

(Continued)

OTHER PUBLICATIONS

Eigler et al., "Cardiac Unloading with an Implantable Interatrial Shunt in Heart Failure: Serial Observations in an Ovine Model of Ischemic Cardiomyopathy", Structural Heart, vol. 1, No. (1-2), 2017, pp. 40-48.

(Continued)

*Primary Examiner* — Susan S Su
*Assistant Examiner* — Erin A Kim

(57) ABSTRACT

An implantable medical device comprising a first frame component. The first frame component including a first set of elongate elements configured to conform to an anatomy of a patient. The implantable medical device also comprising a second frame component including a second set of elongate elements configured to conform to an anatomy of a patient. The first frame component and the second frame component being discrete and separate from one another. The implantable medical device also comprising a conduit
(Continued)

portion arranged between the first frame component and the second frame component. The conduit portion including a membrane connecting the first frame component and the second frame component.

14 Claims, 23 Drawing Sheets

(58) Field of Classification Search
CPC ........... A61B 2017/00575; A61B 2017/00597; A61B 2017/00606; A61B 2017/1139
See application file for complete search history.

(56) References Cited

U.S. PATENT DOCUMENTS

| | | | |
|---|---|---|---|
| 4,443,511 | A | 4/1984 | Worden et al. |
| 5,026,513 | A | 6/1991 | House et al. |
| 5,183,545 | A | 2/1993 | Branca et al. |
| 5,276,276 | A | 1/1994 | Gunn |
| 5,334,217 | A | 8/1994 | Das |
| 5,476,589 | A | 12/1995 | Bacino |
| 5,683,411 | A | 11/1997 | Kavteladze et al. |
| 5,804,011 | A | 9/1998 | Dutta et al. |
| 5,824,055 | A | 10/1998 | Spiridigliozzi et al. |
| 5,944,738 | A | 8/1999 | Amplatz et al. |
| 6,042,602 | A | 3/2000 | Wells |
| 6,042,605 | A | 3/2000 | Martin et al. |
| 6,077,291 | A | 6/2000 | Das |
| 6,080,182 | A | 6/2000 | Shaw et al. |
| 6,461,665 | B1 | 10/2002 | Scholander |
| 6,563,424 | B1 | 5/2003 | Kaario |
| 6,616,675 | B1 | 9/2003 | Evard et al. |
| 6,911,037 | B2 | 6/2005 | Gainor et al. |
| 6,926,670 | B2 | 8/2005 | Rich et al. |
| 7,001,409 | B2 | 2/2006 | Amplatz |
| 7,049,380 | B1 | 5/2006 | Chang et al. |
| 7,236,821 | B2 | 6/2007 | Cates et al. |
| 7,306,729 | B2 | 12/2007 | Bacino et al. |
| 7,462,675 | B2 | 12/2008 | Chang et al. |
| 7,871,659 | B2 | 1/2011 | Cook et al. |
| 7,887,562 | B2 | 2/2011 | Young et al. |
| 7,901,702 | B2 | 3/2011 | Schwarz |
| 7,932,184 | B2 | 4/2011 | Ishii |
| 8,021,331 | B2 | 9/2011 | Herweck et al. |
| 8,043,360 | B2 | 10/2011 | McNamara et al. |
| 8,048,440 | B2 | 11/2011 | Chang et al. |
| 8,091,556 | B2 | 1/2012 | Keren et al. |
| 8,480,707 | B2 | 7/2013 | Pavcnik et al. |
| 8,545,525 | B2 | 10/2013 | Surti et al. |
| 8,696,693 | B2 | 4/2014 | Najafi et al. |
| 8,715,300 | B2 | 5/2014 | Najafi et al. |
| 8,728,103 | B2 | 5/2014 | Surti et al. |
| 8,818,478 | B2 | 8/2014 | Scheffler et al. |
| 9,241,695 | B2 | 1/2016 | Peavey et al. |
| 9,314,556 | B2 | 4/2016 | Tuseth |
| 9,358,371 | B2 | 6/2016 | McNamara et al. |
| 9,399,085 | B2 | 7/2016 | Cleek et al. |
| 9,441,088 | B2 | 9/2016 | Sbriglia et al. |
| 9,456,812 | B2 | 10/2016 | Finch et al. |
| 9,545,300 | B2 | 1/2017 | Cully et al. |
| 9,554,786 | B2 | 1/2017 | Carley et al. |
| 9,629,715 | B2 | 4/2017 | Nitzan et al. |
| 9,636,094 | B2 | 5/2017 | Aurilia et al. |
| 9,649,481 | B2 | 5/2017 | Sadanand |
| 9,681,948 | B2 | 6/2017 | Levi et al. |
| 9,757,107 | B2 | 9/2017 | McNamara et al. |
| 9,775,591 | B2 | 10/2017 | DeLgado et al. |
| 9,849,629 | B2 | 12/2017 | Zaggl et al. |
| 9,861,346 | B2 | 1/2018 | Callaghan |
| 9,878,162 | B2 | 1/2018 | Mika et al. |
| 9,926,416 | B2 | 3/2018 | Sbriglia |
| 9,932,429 | B2 | 4/2018 | Sbriglia |
| 9,949,728 | B2 | 4/2018 | Cahill |
| 10,555,812 | B2 | 2/2020 | Duffy et al. |
| 10,806,458 | B2 | 10/2020 | Todd |
| 12,053,381 | B2 | 8/2024 | Cole et al. |
| 2002/0169475 | A1 | 11/2002 | Gainor et al. |
| 2002/0173742 | A1 | 11/2002 | Keren et al. |
| 2003/0139819 | A1 | 7/2003 | Beer et al. |
| 2004/0063805 | A1 | 4/2004 | Pacetti et al. |
| 2004/0073242 | A1 | 4/2004 | Chanduszko |
| 2004/0173978 | A1 | 9/2004 | Bowen et al. |
| 2004/0267306 | A1 | 12/2004 | Blaeser et al. |
| 2005/0049675 | A1 | 3/2005 | Wallace |
| 2006/0009800 | A1 | 1/2006 | Christianson et al. |
| 2006/0100687 | A1 | 5/2006 | Fahey et al. |
| 2006/0198866 | A1 | 9/2006 | Chang et al. |
| 2007/0244518 | A1 | 10/2007 | Callaghan |
| 2007/0282430 | A1 | 12/2007 | Thommen et al. |
| 2008/0143080 | A1 | 6/2008 | Burr |
| 2008/0249562 | A1 | 10/2008 | Cahill |
| 2008/0262518 | A1 | 10/2008 | Freudenthal |
| 2009/0024042 | A1 | 1/2009 | Nunez et al. |
| 2009/0099640 | A1 | 4/2009 | Weng |
| 2009/0221923 | A1 | 9/2009 | Uemura et al. |
| 2009/0227165 | A1 | 9/2009 | Imai |
| 2009/0264988 | A1 | 10/2009 | Mafi et al. |
| 2010/0049313 | A1 | 2/2010 | Alon et al. |
| 2010/0094401 | A1 | 4/2010 | Kolbel et al. |
| 2011/0071623 | A1 | 3/2011 | Finch et al. |
| 2011/0071624 | A1 | 3/2011 | Finch et al. |
| 2011/0098767 | A1 | 4/2011 | Sugimachi et al. |
| 2011/0153010 | A1 | 6/2011 | Hanna |
| 2011/0167547 | A1 | 7/2011 | Jain |
| 2011/0184439 | A1 | 7/2011 | Anderson et al. |
| 2011/0257723 | A1 | 10/2011 | McNamara |
| 2011/0295183 | A1 | 12/2011 | Finch et al. |
| 2011/0295366 | A1 | 12/2011 | Finch et al. |
| 2012/0136385 | A1 | 5/2012 | Cully |
| 2012/0165928 | A1 | 6/2012 | Nitzan et al. |
| 2012/0265296 | A1 | 10/2012 | McNamara et al. |
| 2013/0165967 | A1 | 6/2013 | Amin et al. |
| 2013/0178784 | A1 | 7/2013 | McNamara et al. |
| 2013/0183515 | A1 | 7/2013 | White |
| 2013/0281988 | A1 | 10/2013 | Magnin et al. |
| 2014/0012368 | A1* | 1/2014 | Sugimoto .......... A61B 17/0057 623/2.11 |
| 2014/0018911 | A1 | 1/2014 | Zhou et al. |
| 2014/0107437 | A1 | 4/2014 | Pinsky |
| 2014/0128795 | A1 | 5/2014 | Keren et al. |
| 2014/0142617 | A1 | 5/2014 | Larsen et al. |
| 2014/0207153 | A1 | 7/2014 | Najafi et al. |
| 2014/0214149 | A1 | 7/2014 | Kuraguntla et al. |
| 2014/0222040 | A1 | 8/2014 | Park et al. |
| 2014/0343670 | A1 | 11/2014 | Bakis et al. |
| 2015/0039084 | A1 | 2/2015 | Levi et al. |
| 2015/0142049 | A1 | 5/2015 | Delgado et al. |
| 2015/0148731 | A1* | 5/2015 | McNamara ........ A61B 17/0057 604/9 |
| 2015/0313595 | A1 | 11/2015 | Houghton et al. |
| 2015/0313596 | A1 | 11/2015 | Todd |
| 2015/0313599 | A1 | 11/2015 | Johnson et al. |
| 2016/0032069 | A1 | 2/2016 | Sbriglia |
| 2016/0038083 | A1 | 2/2016 | Ding et al. |
| 2016/0045199 | A1 | 2/2016 | Mooney |
| 2016/0058452 | A1 | 3/2016 | Brenneman et al. |
| 2016/0120471 | A1 | 5/2016 | Hexels |
| 2016/0167291 | A1 | 6/2016 | Zagl et al. |
| 2016/0331566 | A1 | 11/2016 | Kheradvar et al. |
| 2016/0338706 | A1 | 11/2016 | Rowe |
| 2017/0028194 | A1 | 2/2017 | Bonner et al. |
| 2017/0042705 | A1 | 2/2017 | Cook et al. |
| 2017/0105711 | A1 | 4/2017 | Masters |
| 2017/0106176 | A1 | 4/2017 | Taft et al. |
| 2017/0172766 | A1 | 6/2017 | Vong et al. |
| 2017/0196673 | A1 | 7/2017 | Cully et al. |
| 2017/0224323 | A1 | 8/2017 | Rowe et al. |
| 2017/0281339 | A1 | 10/2017 | Levi et al. |
| 2017/0319823 | A1 | 11/2017 | Yacoby et al. |
| 2017/0329425 | A1 | 11/2017 | Karagozler et al. |
| 2018/0000580 | A1 | 1/2018 | Wallace et al. |
| 2018/0000584 | A1 | 1/2018 | Duffy et al. |
| 2018/0055629 | A1 | 3/2018 | Oba et al. |

(56) References Cited

U.S. PATENT DOCUMENTS

| | | | |
|---|---|---|---|
| 2018/0098772 | A1 | 4/2018 | Goldshtein et al. |
| 2018/0242912 | A1 | 8/2018 | Amimori et al. |
| 2018/0280667 | A1 | 10/2018 | Keren |
| 2019/0021407 | A1 | 1/2019 | Howland |
| 2019/0086278 | A1 | 3/2019 | Casillas et al. |
| 2019/0116892 | A1 | 4/2019 | Scheffler et al. |
| 2019/0132948 | A1 | 5/2019 | Longinotti-Buitoni et al. |
| 2019/0231510 | A1 | 8/2019 | Rafiee et al. |
| 2019/0282178 | A1 | 9/2019 | Volosin et al. |
| 2019/0364983 | A1 | 12/2019 | Nakajima et al. |
| 2020/0038567 | A1 | 2/2020 | Siess et al. |
| 2020/0085600 | A1 | 3/2020 | Schwartz et al. |
| 2020/0179663 | A1 | 6/2020 | McDaniel et al. |
| 2020/0196876 | A1 | 6/2020 | Minor et al. |
| 2020/0196943 | A1 | 6/2020 | Minor et al. |
| 2020/0196944 | A1 | 6/2020 | Minor et al. |
| 2020/0197178 | A1 | 6/2020 | Vecchio |
| 2020/0281484 | A1 | 9/2020 | Wong |
| 2021/0195732 | A1 | 6/2021 | Longinotti-Buitoni et al. |
| 2021/0243890 | A1 | 8/2021 | Edmundson et al. |
| 2021/0259839 | A1 | 8/2021 | Cole et al. |
| 2021/0290214 | A1 | 9/2021 | Cole et al. |
| 2022/0240600 | A1 | 8/2022 | Deilmann et al. |
| 2023/0116796 | A1 | 4/2023 | Cole et al. |

FOREIGN PATENT DOCUMENTS

| | | | |
|---|---|---|---|
| CN | 103458832 | A | 12/2013 |
| CN | 104414692 | A | 3/2015 |
| CN | 106413586 | A | 2/2017 |
| CN | 106456181 | A | 2/2017 |
| CN | 106659501 | A | 5/2017 |
| CN | 107249482 | A | 10/2017 |
| CN | 107920812 | A | 4/2018 |
| CN | 115003232 | A | 9/2022 |
| EP | 2637576 | A1 | 9/2013 |
| EP | 3061598 | A1 | 8/2016 |
| EP | 3117848 | A1 | 1/2017 |
| EP | 3563703 | A1 | 11/2019 |
| GB | 1355373 | A | 6/1974 |
| GB | 1506432 | A | 4/1978 |
| GB | 1509023 | A | 4/1978 |
| JP | 07-502918 | A | 3/1995 |
| JP | 2000-505316 | A | 5/2000 |
| JP | 2001-519694 | A | 10/2001 |
| JP | 2002-248105 | A | 9/2002 |
| JP | 2005-528181 | A | 9/2005 |
| JP | 2008-512139 | A | 4/2008 |
| JP | 2008-512211 | A | 4/2008 |
| JP | 2010-505481 | A | 2/2010 |
| JP | 2012-500665 | A | 1/2012 |
| JP | 2012-214968 | A | 11/2012 |
| JP | 2013-517890 | A | 5/2013 |
| JP | 2014-503246 | A | 2/2014 |
| JP | 2016-511656 | A | 4/2016 |
| JP | 2016-518948 | A | 6/2016 |
| JP | 2017-513545 | A | 6/2017 |
| JP | 2017-515631 | A | 6/2017 |
| JP | 2017-517307 | A | 6/2017 |
| JP | 2017-187499 | A | 10/2017 |
| JP | 2019-014978 | A | 1/2019 |
| JP | 2021-523568 | A | 9/2021 |
| JP | 2021-531097 | A | 11/2021 |
| WO | 93/13712 | A1 | 7/1993 |
| WO | 97/27898 | A1 | 8/1997 |
| WO | 98/42276 | A1 | 10/1998 |
| WO | 2003/103476 | A2 | 12/2003 |
| WO | 2004/091411 | A2 | 10/2004 |
| WO | 2008/040555 | A2 | 4/2008 |
| WO | 2009/137755 | A2 | 11/2009 |
| WO | 2010/022138 | A2 | 2/2010 |
| WO | 2011/093941 | A2 | 8/2011 |
| WO | 2012/071075 | A1 | 5/2012 |
| WO | 2012/091809 | A1 | 7/2012 |
| WO | 2014/018977 | A1 | 1/2014 |
| WO | 2014/150106 | A1 | 9/2014 |
| WO | 2014/189977 | A1 | 11/2014 |
| WO | 2015/109027 | A2 | 7/2015 |
| WO | 2015/168501 | A2 | 11/2015 |
| WO | 2015/168507 | A1 | 11/2015 |
| WO | 2016/135188 | A1 | 9/2016 |
| WO | 2017/118738 | A1 | 7/2017 |
| WO | 2018/123034 | A1 | 7/2018 |
| WO | 2019/216885 | A1 | 11/2019 |
| WO | 2019/217503 | A1 | 11/2019 |
| WO | 2020/018697 | A1 | 1/2020 |
| WO | 2021/009489 | A1 | 1/2021 |

OTHER PUBLICATIONS

Feldman et al., "Transcatheter Interatrial Shunt Device for the Treatment of Heart Failure Rationale and Design of the Randomized Trial to Reduce Elevated Left Atrial Pressure in Heart Failure (Reduce LAP-HF I)", Circulation Heart failure, vol. 9, No. 7, 2016, pp. 1-10.

Gregg et al., "Interatrial Shunting for Heart Failure The V-Wave Shunt", Presentation at the Transcatheter Cardiovascular Therapeutics (TCT) Congress in Denver, Colorado, 2017, 18 pages.

International Preliminary Report on Patentability received for PCT Patent Application No. PCT/US2021/013411, mailed on Jul. 28, 2022, 9 pages.

International Search Report and Written Opinion received for PCT Patent Application No. PCT/US2021/013411, mailed on May 6, 2021, 11 pages.

Søndergaard et al., "Transcatheter treatment of heart failure with preserved or mildly reduced ejection fraction using a novel interatrial implant to lower left atrial pressure", European Journal of Heart Failure, vol. 16, 2014, pp. 796-801.

Stoppa et al., "Wearable Electronics and Smart Textiles: A Critical Review", Sensors 2014, vol. 14, No. 7, pp. 11957-11992.

Wei, X., Liu, X., Rosenzweig, A. What do we know about the cardiac benefits of exercise? Trends in Cardiovascular Medicine; 25(6): 537-539. Aug. 2015 (Year: 2015).

* cited by examiner

MEDICAL DEVICES FOR SHUNTS, OCCLUDERS, FENESTRATIONS AND RELATED SYSTEMS AND METHODS

CROSS-REFERENCE TO RELATED APPLICATION

This application is a national phase application of PCT Application No. PCT/US2021/013411, internationally filed on Jan. 14, 2021, which claims the benefit of Provisional Application No. 62/962,541, filed Jan. 17, 2020, which are incorporated herein by reference in their entireties for all purposes.

FIELD

The present disclosure relates generally to implantable medical devices, and more specifically to implantable medical devices for shunting and/or occluding bodily fluids or structures and related systems and methods thereof.

BACKGROUND

Heart failure and diseases of the heart affect millions of people worldwide. Heart failure includes failure of either the left side of the heart, the right side of the heart, or both. Diseases of the heart that can lead to heart failure include hypertension, pulmonary arterial hypertension, and congenital defects of the heart. The constantly evolving nature of heart failure represents a significant challenge for the treatment methods. Therefore, there is a need for new and adaptable methods and devices for treating heart failure.

SUMMARY

According to one example ("Example 1"), an implantable medical device, includes a first frame component configured to conform to an anatomy of a patient; a second frame component configured to conform to an anatomy of a patient wherein the first frame component and the second frame component are discrete and separate from one another, and at least one of the first frame component and the second frame component includes inner apices and outer apices, and one or more eyelets arranged with at least one of the outer apices and the inner apices; and a conduit portion arranged between the first frame component and the second frame component, the conduit portion including a membrane connecting the first frame component and the second frame component.

According to another example ("Example 2"), further to the device of Example 1, at least a portion of the conduit portion is radially unsupported by the first and second frame components within the conduit portion.

According to another example ("Example 3"), further to the device of Example 2, the first and second frame components are configured to facilitate deployment of the conduit portion and maintaining a lumen through the conduit portion.

According to another example ("Example 4"), further to the device of any one of Examples 1-3, the conduit portion is free of frame components.

According to another example ("Example 5"), further to the device of any one of Examples 1-4, the first frame component includes a first set of elongate elements and the second frame component includes a second set of elongate elements, and the first set of elongate elements and the second set of elongate elements are non-contiguous with one another.

According to another example ("Example 6"), further to the device of Example 5, the first set of elongate elements include a first plurality of support struts and wherein the second set of elongate elements include a second plurality of support struts, the first and second plurality of support struts forming a support structure within each of the elongate elements.

According to another example ("Example 7"), further to the device of Example 6, the first set of elongate elements form a plurality of first lobes.

According to another example ("Example 8"), further to the device of Example 6, the first set of elongate elements form a star shape.

According to another example ("Example 9"), further to the device of any one of Examples 1-8, at least one of the first frame component and the second frame component includes a star shape having the inner apices and the outer apices.

According to another example ("Example 10"), further to the device of Example 9, the one or more eyelets includes a pair of eyelets arranged on either side at least one of the inner apices.

According to another example ("Example 11"), further to the device of any one of Examples 1-8, at least one of the first frame component and the second frame component includes a star shape having a first surface and a second surface and eyelets extending about the frame element along one or both of the first surface and the second surface.

According to another example ("Example 12"), further to the device of Example 11, the eyelets extend about the frame element and are arranged alternatively on the first surface and the second surface.

According to another example ("Example 13"), further to the device of any one of Examples 1-8, at least one of the inner apices and the outer apices include one or more greater width portions and one or more lesser width portions arranged between the at least one of the inner apices and the outer apices.

According to another example ("Example 14"), further to the device of Example 13, at least one of the first frame component and the second frame component includes two greater width portions and one lesser width portion in between two apices of the apices.

According to another example ("Example 15"), further to the device of Example 14, the eyelets are arranged with the one or more greater width portions.

According to another example ("Example 16"), further to the device of any one of Examples 1-8, at least one of the first frame component and the second frame component includes a first surface and a second surface and openings between the first surface and the second surface.

According to another example ("Example 17"), further to the device of any one of Examples 1-8, the device also includes one or more tethers coupled to the first frame component and the second frame component and arranged through the conduit portion.

According to another example ("Example 18"), further to the device of Example 17, the one or more tethers are configured to structurally enhance the conduit portion.

According to another example ("Example 19"), further to the device of any one of Examples 1-8, at least one of the first frame component and the second frame component includes a curved star shape.

According to another example ("Example 20"), further to the device of any one of Examples 1-8, at least one of the first frame component and the second frame component includes apices, eyelets arranged at the apices, a tether arranged through and connecting the eyelets.

According to another example ("Example 21"), further to the device of any one of Examples 1-8, the membrane includes a first layer and a second layer that sandwich the first frame component and the second frame component.

According to another example ("Example 22"), further to the device of any one of Examples 1-8, at least one of the first frame component and the second frame component includes a fan shape.

According to another example ("Example 23"), further to the device of any one of Examples 1-8, at least one of the first frame component and the second frame component includes a partial star shape.

According to another example ("Example 24"), further to the device of any one of Examples 1-8, at least one of the first frame component and the second frame component includes at least one elongate element that overlap upon itself to form one or more loops and the one or more loops form the eyelets.

According to another example ("Example 25"), a method for regulating blood pressure between a left and right atrium of a heart includes delivering the implantable medical device to a desired treatment location within a body of a patient, the implantable medical device including a conduit portion configured to span a septum of the heart and configured to allow fluid flow therethrough; a frame component including a first set of elongate elements arranged on a first side of the conduit portion and a second set of elongate elements arranged on a second side of the conduit portion with the first set of elongate elements and the second set of elongate elements being non-contiguous with one another, and at least one of the first frame component and the second frame component includes inner apices and outer apices, and one or more eyelets arranged with at least one of the outer apices and the inner apices; positioning the device such that the conduit portion spans a septum between the left and right atrium of the heart; and deploying the first frame component and the second frame component such that the conduit portion opens a desired amount to provide a fluid flow path between the left and right atrium.

According to another example ("Example 26"), further to the method of Example 25, the method also includes adjusting tension on the device to adjust a diameter of the conduit portion and a fluid flow velocity therethrough.

According to one example ("Example 27"), an implantable medical device includes a first frame component configured to conform to an anatomy of a patient; a second frame component configured to conform to an anatomy of a patient wherein at least one of the first frame component and the second frame component includes inner apices and outer apices, and one or more eyelets arranged with at least one of the outer apices and the inner apices; and wherein at least one of the first frame component and the second frame component includes a star shape having the inner apices and the outer apices and the one or more eyelets includes a plurality of eyelets pairs with one of the plurality of eyelet pairs arranged on either side of each of at least one of the inner apices and the outer apices.

According to another example ("Example 28"), further to the implantable medical device of Example 27, the plurality of eyelets pairs are arranged on a first side of the inner apices.

According to another example ("Example 29"), further to the implantable medical device of Example 27, the plurality of eyelets pairs include a first plurality of eyelet pairs each arranged adjacent the inner apices and a second plurality of eyelet pairs each arranged adjacent the outer apices.

According to another example ("Example 30"), further to the implantable medical device of Example 29, the first plurality of eyelet pairs each arranged on a first side of the at least one of the first frame component and the second frame component adjacent the inner apices and the second plurality of eyelet pairs each arranged on a second side of the at least one of the first frame component and the second frame component adjacent the outer apices.

According to another example ("Example 31"), further to the implantable medical device of Example 27, at least one of the first frame component and the second frame includes a first surface and a second surface, and the plurality of eyelet pairs extend about the frame element along one or both of the first surface and the second surface.

According to another example ("Example 32"), further to the implantable medical device of Example 31, the plurality of eyelet pairs extend about the frame element and are arranged alternatively on the first surface and the second surface.

According to another example ("Example 33"), further to the implantable medical device of Example 27, at least one of the inner apices and the outer apices include one or more greater width portions and one or more lesser width portions arranged between the at least one of the inner apices and the outer apices.

According to another example ("Example 34"), further to the implantable medical device of Example 33, at least one of the first frame component and the second frame component includes two greater width portions and one lesser width portion in between two apices of the apices.

According to another example ("Example 35") further to the implantable medical device of Example 34, wherein the plurality of eyelet pairs are arranged with the one or more greater width portions.

According to another example ("Example 36"), further to the implantable medical device of any one of Examples 27-35, the implantable medical device also includes a conduit portion arranged between the first frame component and the second frame component and one or more tethers coupled to the first frame component and the second frame component and arranged through the conduit portion.

According to another example ("Example 37"), further to the implantable medical device of Example 36, the one or more tethers are configured to structurally enhance the conduit portion.

According to another example ("Example 38"), further to the implantable medical device of any one of Examples 27-37, the implantable medical device also includes a membrane includes a first layer and a second layer that sandwich the first frame component and the second frame component.

According to one example ("Example 39"), an implantable medical device includes a first frame component configured to conform to an anatomy of a patient; a second frame component configured to conform to an anatomy of a patient wherein at least one of the first frame component and the second frame component includes inner apices and outer apices, and one or more eyelets arranged with at least one of the outer apices and the inner apices; and wherein at least one of the first frame component and the second frame component includes a first surface and a second surface and openings between the first surface and the second surface.

According to another example ("Example 40"), further to the implantable medical device of Example 39, the implantable medical device also includes a conduit portion arranged between the first frame component and the second frame component and one or more tethers coupled to the first frame component and the second frame component and arranged through the conduit portion.

According to another example ("Example 41"), further to the implantable medical device of Example 40, the one or more tethers are configured to structurally enhance the conduit portion.

According to one example ("Example 42"), an implantable medical device includes a first frame component configured to conform to an anatomy of a patient; a second frame component configured to conform to an anatomy of a patient wherein at least one of the first frame component and the second frame component includes inner apices and outer apices, and one or more eyelets arranged with at least one of the outer apices and the inner apices; and wherein the first frame component and the second frame component includes apices, eyelets arranged at the apices, a tether arranged through and connecting the eyelets of the first frame component and the eyelets of the second frame component.

According to one example ("Example 43"), an implantable medical device includes a first frame component configured to conform to an anatomy of a patient; a second frame component configured to conform to an anatomy of a patient wherein at least one of the first frame component and the second frame component includes inner apices and outer apices, and one or more eyelets arranged with at least one of the outer apices and the inner apices; and a membrane includes a first layer and a second layer that sandwich the first frame component and the second frame component.

According to one example ("Example 44"), an implantable medical device includes a first frame component configured to conform to an anatomy of a patient; a second frame component configured to conform to an anatomy of a patient wherein at least one of the first frame component and the second frame component includes inner apices and outer apices, and one or more eyelets arranged with at least one of the outer apices and the inner apices; and at least one of the first frame component and the second frame component includes a fan shape.

According to one example ("Example 45"), an implantable medical device includes a first frame component configured to conform to an anatomy of a patient; a second frame component configured to conform to an anatomy of a patient wherein at least one of the first frame component and the second frame component includes inner apices and outer apices, and one or more eyelets arranged with at least one of the outer apices and the inner apices; and wherein at least one of the first frame component and the second frame component includes a partial star shape.

According to one example ("Example 46"), an implantable medical device includes a first frame component configured to conform to an anatomy of a patient; a second frame component configured to conform to an anatomy of a patient wherein at least one of the first frame component and the second frame component includes inner apices and outer apices, and one or more eyelets arranged with at least one of the outer apices and the inner apices; and wherein at least one of the first frame component and the second frame component includes at least one elongate element that overlap upon itself to form one or more loops and the one or more loops form the eyelets.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Definitions and Terminology

Figure 1:
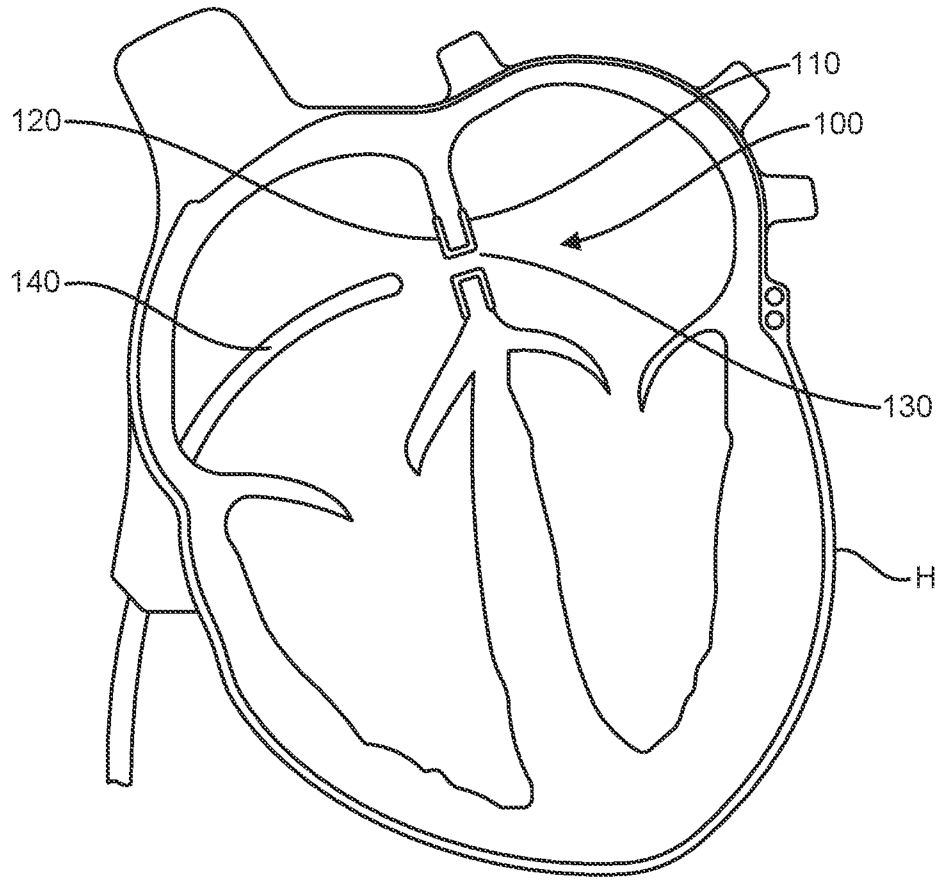
FIG. 1 is an example implantable medical device for regulating blood pressure in accordance with an embodiment.

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters in view of differences in measurements associated with other components, particular implementation scenarios, imprecise adjustment and/or manipulation of objects by a person or machine, and/or the like, for example. In the event it is determined that individuals having ordinary skill in the relevant arts would not readily ascertain values for such reasonably small differences, the terms "about" and "approximately" can be understood to mean plus or minus 10% of the stated value.

DESCRIPTION OF VARIOUS EMBODIMENTS

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Various aspects of the present disclosure are directed toward two implantable medical devices such as device for shunting and/or occluding bodily fluids or structures. In certain instances, the various aspects of the present disclosure relate to methods and devices for treating heart failure by reducing elevated blood pressure in a heart chamber by creating a pressure relief shunt. Additionally, some embodiments relate to methods and devices for customizing, adjusting or manipulating the flow of blood through the shunt in order to enhance the therapeutic effect of the pressure relief shunt.

FIG. 1 is an example implantable medical device for regulating blood pressure in accordance with an embodiment. The implantable medical device 100 is shown implanted within a heart H of a patient. The device 100 is shown arranged between the patient's left atrium and right atrium. In certain instances, the device 100 may be used to regulate blood flow within the heart H, for example, between the left and right atriums LA, RA. As shown, the device 100 generally includes a first frame component 110 arranged on a first side of a septum (e.g., within the right atrium RA), a second frame component 120 arranged on a second side of the septum (e.g., within the left atrium LA), and a conduit portion 130 extending through the septum. A needle may be used to create an opening in the septum.

A sheath 140 and constraining and/or release lines (not shown) may be used to facilitate deployment of the device 100. For example, a first side of the device 100 that includes the first frame component 110 may be released after the sheath 140 is advanced through the septum and to the RA, and the second frame component 120 that includes the second frame component 120 may be released on the LA side of the septum. A conduit portion 130 (e.g., shown in FIG. 2) is arranged within the opening. The frame components 110, 120 and the conduit portion 130 may be compressed within the sheath 140 during delivery of the device 100 to the desired treatment area within the patient and subsequently expanded during deployment of the device 100.

Figure 2:
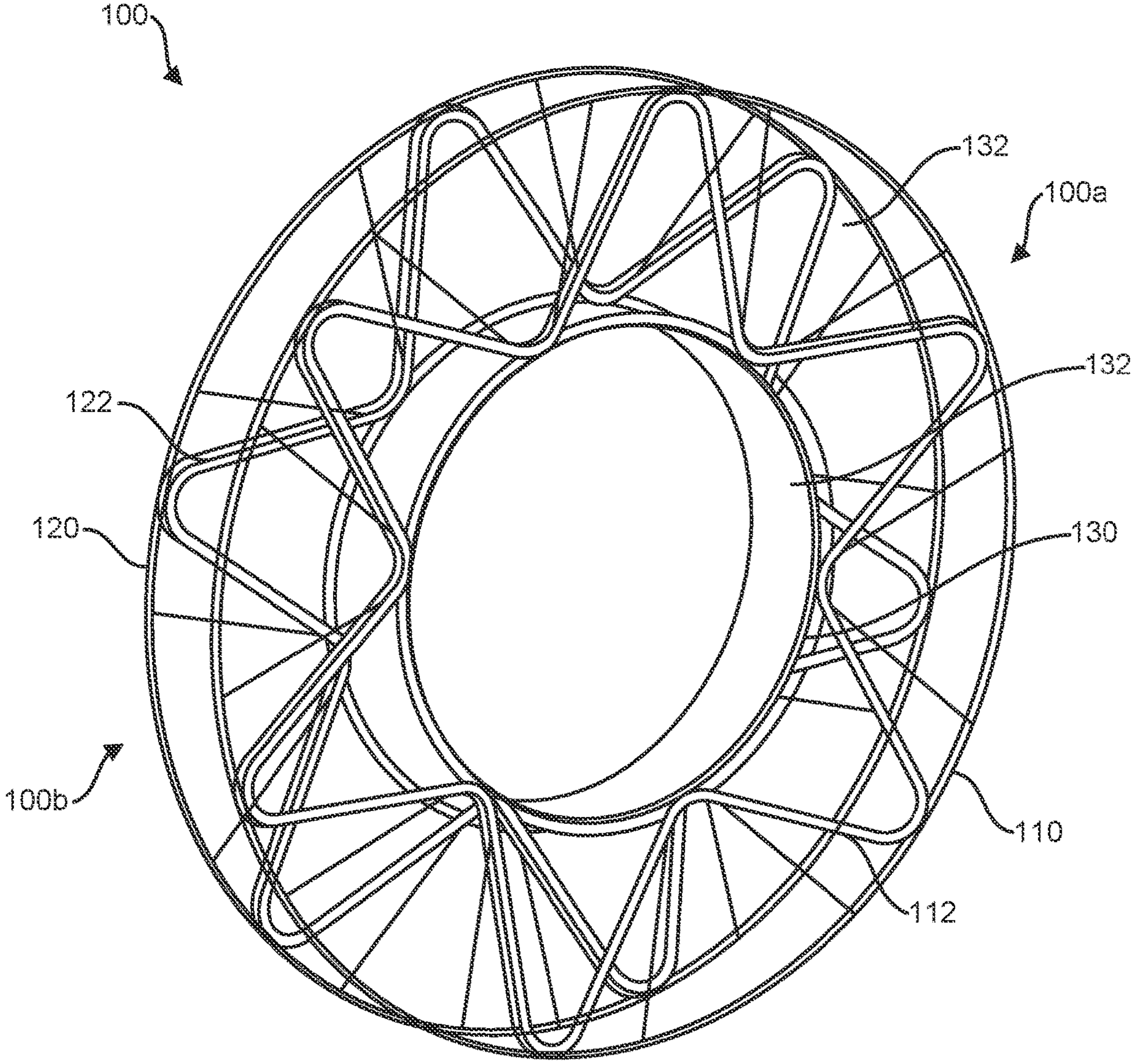
FIG. 2 is an example implantable medical device for regulating blood pressure in accordance with an embodiment.

FIG. 2 is an example implantable medical device for regulating blood pressure in accordance with an embodiment. As shown, the device 100 includes the first frame component 110 and the second frame component 120. The first frame component 110 may be configured to conform to the patient's anatomy (i.e., the first side of the septum, for example). The second frame component 120 may be configured to conform to the patient's anatomy (i.e., the second side of the septum).

In certain instances, the first frame component 110 includes a first set of elongate elements 112, and the second frame component 120 includes a second set of elongate elements 122. The frame components 110, 120, including and for example the elongate elements 112, 122, may be discrete and separate from one another. For example, the first frame component 110 forms a first side 100*a* of the device 100 and the second frame component 120 forms a second side 100*b* of the device 100. The first frame component 110 being discrete and separate from the second frame component 120 does not enter into the second side 100*b* of the device and the second frame component 120 being discrete and separate from the first frame component 110 does not enter into the first side 100*a* of the device.

In certain instances, the first and second frame components 110, 120 are non-contiguous with one another. The first and second frame components 110, 120 being non-contiguous with one another allows the first and second frame components 110, 120 to be distinct and separate from one another. In addition, the first and second frame components 110, 120 are free to move, in response to movement of the patient's anatomy, separate from one another. In this manner, forces acting on one of the first and second frame components 110, 120 are maintained within the other of the first and second frame components 110, 120. The forces acting on one of the first and second frame components 110, 120 may be isolated to the frame component to which the force is acted on.

As shown, the conduit portion 130 is arranged between the first frame component and the second frame component. At least a portion of the conduit portion 130 is generally radially or circumferentially unsupported by the first and second frame components 110, 120 within the conduit portion 130. As shown in FIG. 2, the conduit portion 130 transitions to the first side 100*a* and the second side 100*b* at approximately a 90 degree angle (other angles are contemplated). Bounds of the conduit portion 130 may be considered to be a location at which the conduit portion 130 transitions to the first side 100*a* and the second side 100*b*. The first and second frame components 110, 120 extend laterally relative to the conduit portion 130. In addition, the first and second frame components 110, 120 may support the conduit portion 130 without substantially entering the bounds of the conduit portion 130. In certain instances, the first and second frame components 110, 120 support the conduit portion 130 laterally from outside of bounds the conduit portion 130. Thus, the first and second frame components 110, 120 may maintain a lumen through the conduit portion 130 and facilitate deployment of the conduit portion 130 by laterally forcing the conduit portion 130 open.

In certain instances, the first and second frame components 110, 120 may impart tension to the conduit portion 130 to deploy and maintain the conduit portion 130 with a lumen therethrough. The conduit portion 130 may be deployed within the septum between tissue surfaces through an opening (e.g., needle stick across the septum) that has a diameter smaller than a fully deployed diameter of the conduit portion 130. Tension in the conduit portion 130 imparted by expansion of the first and second frame components 110, 120 may also expand the septum between tissue surfaces to a desired shunt size.

In certain instances, the conduit portion 130 may be substantially free of frame components. For example, because the first and second frame components 110, 120 are non-contiguous with one another, as described above, and are arranged external to the bounds of the conduit portion 130. The conduit portion 130 may include, for example, a membrane 132, such as an expanded polytetrafluoroethylene (ePTFE) membrane, connecting the first frame component 110 and the second frame component 120. The membrane 132 generally separates the first frame component 110 and the second frame component 120 by a suitable distance compatible with the patient's body. For example, the membrane 132 can separate the first frame component 110 and the second frame component 120 by a gap of from 0 to 15 mm depending on the desired treatment location within the patient's body. In addition, the conduit portion may be formed of only the membrane 132. The conduit portion 130, which is configured to be deployed within the septum between tissue surfaces, is free of the first frame component 110 and the second frame component 120. The conduit portion 130 may include a smooth interior that facilitates blood flow therethrough without ridges from a stent element interrupting or disrupting flow. Thus, the conduit portion 130 may lessen the opportunity for thrombosis.

In addition to the membrane 132 forming the conduit portion 130, the membrane 132 may also cover at least a portion of the first frame component 110, at least a portion of the second frame component 120, or at least a portion of the first frame component 110 and the second frame component 120. In certain instances, the membrane 132 arranged on at least a portion of the first frame component 110 and/or the second frame component 120 is a separate membrane film (e.g., a first membrane film arranged on first frame component 110 and a second membrane film arranged on the second frame component 120). In these instances, the membrane film or films may be coupled to the membrane 132 in the conduit portion 130. The membrane 132 may be elastic to allow for expansion of the conduit portion 130 and to allow for movement of portions of the first frame component 110 and/or the second frame component 120 (e.g., movement of the first set of elongate elements 112 and/or the second set of elongate elements 122).

The membrane 132 may span gaps between the first set of elongate elements 112 and/or the second set of elongate elements 122. The membrane 132, in certain instances, is arranged on at least a tissue engaging side of the first frame component 110 and a tissue engaging side the second frame component 120. In these instances, the membrane 132 is configured to lessens frame erosion potential of the first frame component 110 and/or the second frame component 120. The membrane 132 and the arrangement of the first set of elongate elements 112 and/or the second set of elongate elements 122 may conform to the tissue surfaces surrounding the septum. The first set of elongate elements 112 and/or the second set of elongate elements 122 may lay flat against the tissue surfaces.

In certain instances, each of the first set of elongate elements 112 may be attached to one another via the membrane 132 to form the first frame component 110. In certain instances, the first frame component 110 may form a substantially flat or 2-dimensional, disc-like shape, as shown. Additionally, or alternatively, the second set of elongate elements 122 may also be attached to one another via the membrane 132 to form the second frame component 120. The second frame component 120 may also form a substantially flat or 2-dimensional, disc-like shape such that the first and second frame components 110, 120 are substantially parallel to one another when the device 100 is in a deployed configuration.

In certain instances, the membrane 132 may be configured to promote tissue ingrowth over at least a portion of the membrane 132, or at least a portion of the membrane 132. In certain instances, the membrane 132 is configured to promote tissue ingrowth to cover at least a portion of the first and/or second frame components 110, 120, which may further promote compatibility and stability of the device 100 within the patient's body. The membrane 132 within the conduit portion 130 may be configured to not allow tissue ingrowth leading to increased patency. In certain instances, the membrane 132 is configured to promote endothelization without obstructive ingrowth within the conduit portion 130. The membrane 132 may promote endothelization without obstructive overgrowth of tissue into the conduit portion 130.

In certain instances, the device 100 may be capable of delivering a drug to the desired treatment location within the patient's body. For example, the device 100 may be capable of eluting a drug configured to modulate tissue response. In certain instances, the device 100 may be coated with a therapeutic coating, drug eluting material or other therapeutic material or a hydrophilic coating. In one specific example, the device 100 can be coated with heparin to facilitate thromboresistance and patency of the device 100. Alternatively, or additionally, the device 100 may include paclitaxel (to modulate tissue/cellular response).

Figure 3A:
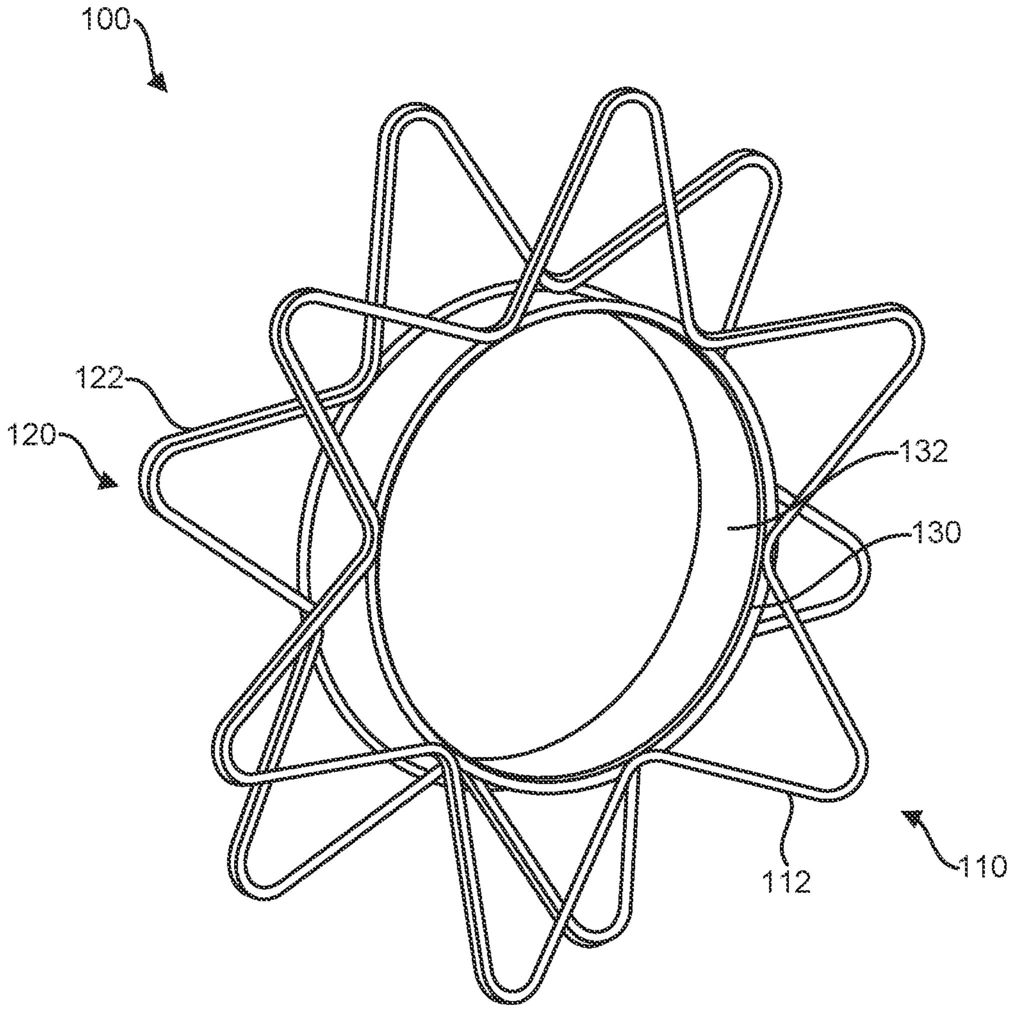
FIG. 3A is a perspective view of another example implantable medical device for regulating blood pressure in accordance with an embodiment.

FIG. 3A is a perspective view of another example implantable medical device 100 for regulating blood pressure in accordance with an embodiment. As shown, each of the first set of elongate elements 112 may be discrete and separate from adjacent elongate elements. In other terms, the membrane 132 does not connect each of the first set of elongate elements 112 together. In this way, each of the first set of elongate elements 112 may move independently from one another and individually conform to the topography of the first side of the septum, thus providing a highly conformable first frame component 110. Each of the second set of elongate elements 122 may also be discrete and separate from adjacent elongate elements. For example, each of the second set of elongate elements 122 may move independently from one another and individually conform to the second side of the septum, much like the first set of elongate elements 112 conforms to the first side of the septum. Thus, both the first and second frame components 110, 120 are highly conformable and may conform independently of one another based on the patient's anatomy.

In certain instances, one of the first or second set of elongate elements 112, 122 of the first and second frame components 110, 120 may be attached to one another via the membrane 132 while the other set of elongate elements are unattached (e.g., they are discrete and separate from adjacent elongate elements). In other instances, only some of the first or second set of elongate elements 112, 122 may be attached to one another, while other elongate elements of the first and second set of elongate elements 112, 122 are not attached. Thus, the device 100 can be highly customizable to the patient depending on the desired treatment location within the patient, and size and/or shape of the defect, among other factors.

The device 100 is generally deployable or expandable from a delivery configuration to the deployed configuration. In some instances, the first set of elongate elements 112 and the second set of elongate elements 122 may nest within one another when the device is in the delivery configuration. This allows the device 100 to compress to a smaller size, for example, for delivery of the device 100 to a wider variety of treatment locations (e.g., through small, narrow, or convoluted passageways).

Figure 3B:
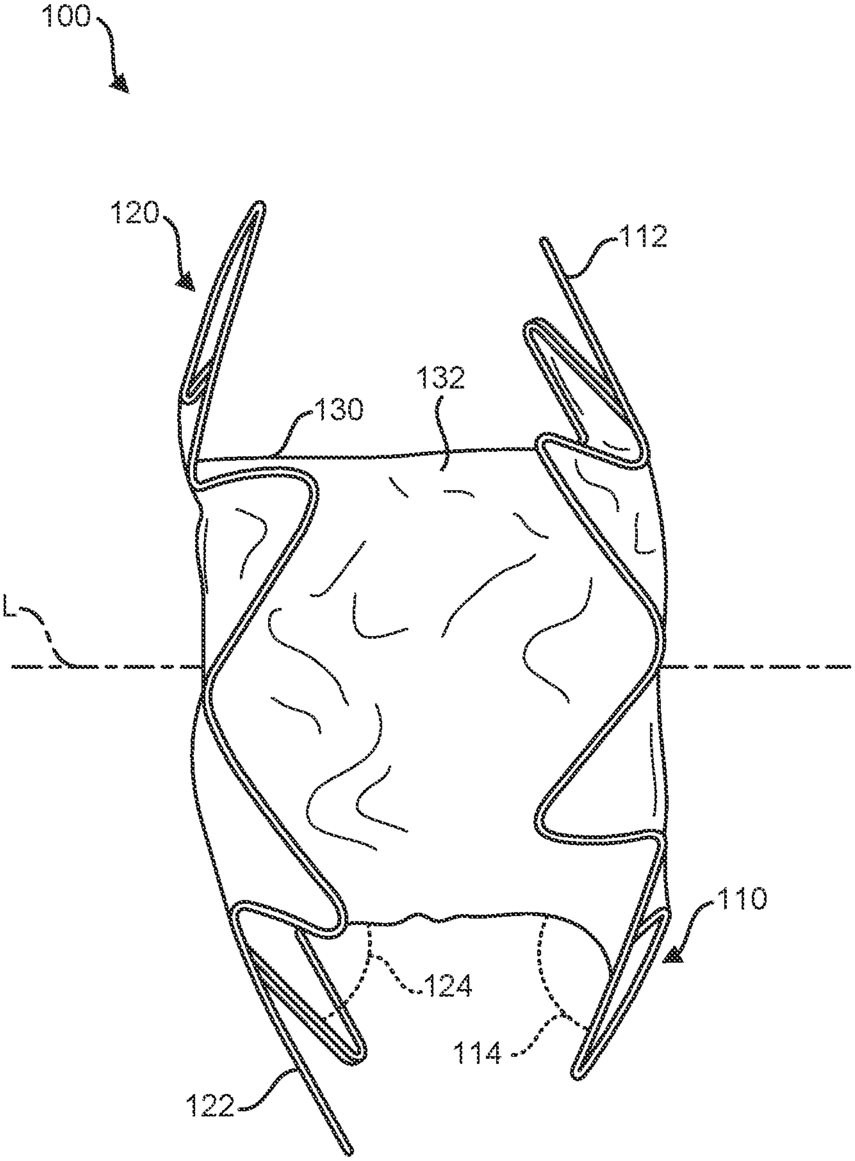
FIG. 3B is a side view of the implantable medical device for regulating blood pressure, shown in FIG. 3A, in accordance with an embodiment.

FIG. 3B is a side view of the implantable medical device for regulating blood pressure, shown in FIG. 3A, in accordance with an embodiment. FIG. 3B shows the device 100 in the deployed configuration. As shown, the first frame component 110 including the first set of elongate elements 112 and the second frame component 120 including the second set of elongate elements 122 are positioned radially outward with respect to a longitudinal axis L of the conduit portion 130 when the device 100 is in the deployed configuration. For example, the first and second frame components 110, 120 are positioned at first and second angles 114, 124, respectively. The first and second angles 114, 124 may form approximately a 90° angle with respect to the longitudinal axis L when the device is in the deployed configuration. This allows the first and second frame components 110, 120 to be positioned parallel with and adjacent to the first and second sides of the septum. In certain instances, the first and second frame components 110, 120 may be positioned at any angle relative to the longitudinal axis L (for example, from about 0° to greater than 90° with respect to the longitudinal axis L) that allows for contact with the tissue surface of the first and second sides of the septum.

In certain instances, the first and second elongate elements 112, 122 are configured to separate from one another when the device 100 is in the deployed configuration. As shown in FIG. 3B, each of the first set of elongate elements 112 are discrete and separate from one another when the device 100 is in the deployed configuration such that each of the first set of elongate elements 112 may move independently from adjacent elongate elements. Each of the second set of elongate elements 122 may also be discrete and separate from one another when the device 100 is in the deployed configuration such that each of the second set of elongate elements 122 move independently from adjacent elongate elements.

The first and second frame components 110, 120 may maintain a lumen through the conduit portion 130 and facilitate deployment of the conduit portion 130 by laterally forcing the conduit portion 130 open. In addition, the lumen may be free or without the first and second frame components 110, 120. In this manner, the conduit portion 130 may facilitate re-crossing of the septum for addition procedures (e.g., left atrial appendage occluder implantation). In addition, the first and second frame components 110, 120 may be differently configured. For example, one of the first and second frame components 110, 120 may be flared while the other of the first and second frame components 110, 120 is flat. In other instances, both the first and second frame components 110, 120 may be flared. In addition, one of the first and second frame components 110, 120 may be convex while the other of the first and second frame components 110, 120 is flat or concave or both the first and second frame components 110, 120 may be convex. Further, one of the first and second frame components 110, 120 may be concave while the other of the first and second frame components 110, 120 is flat or convex or both the first and second frame components 110, 120 may be concave. In addition, the first and second frame components 110, 120 may be different sizes.

The first and second frame components 110, 120 may include a sensor integrated into the respective frame component, for example, for continuous monitoring of various hemodynamic parameters such as pressure, among other parameters, within the patient's body. For example, an antenna or inductor may be wrapped around the perimeter of one of the first and second frame components 110, 120 and the sensor may be attached to the inductor. The sensor may be configured to, for example, sense physiologic properties, such as temperature, electrical signals of the heart, blood chemistry, blood pH level, hemodynamics, biomarkers, sound, pressure, and electrolytes that may be important in diagnosing, monitoring, and/or treating heart disease, heart failure, and/or other cardiovascular disease states In certain instances, the conduit portion 130 may be sizeable after delivery. The membrane 132 may be selectively adjustable by a balloon applied within the conduit portion 130 to distend the membrane 132. The device 100 can be any size suitable to fit the anatomy of the patient. In certain instances, a diameter of the conduit portion is from 3 to 12 mm. For example, the diameter of the conduit portion may be from 4 to 10 mm, or from 5 to 8 mm depending on the anatomy of the patient and/or the desired treatment location. The first and second frame components 110, 120 generally have a larger diameter than that of the conduit portion 130, for example, so that the frame components may anchor the conduit portion 130 of the device 100 within the septum.

The device 100 can be any shape suitable to fit the anatomy of the patient. For example, the first and second frame portions 110, 120 may be any of a variety of suitable shapes for anchoring the device 100 within the patient's body. For example, the first and second frame portions 110, 120 may be substantially circular, ovular, diamond-shaped, star-shaped, flower-shaped, or any other suitable shape as desired. In certain instances, for example, at least one of the first and second set of elongate elements 112, 122 form a star shape. In certain instances, both the first and second set of elongate elements 112, 122 form a star shape.

In certain instances, the first set of elongate elements 112 forms a plurality of first lobes 116 and the second set of elongate elements 122 forms a plurality of second lobes 126. Each of the plurality of first and second lobes 116, 126 may include, for example, from 3 to 12 lobes, from 4 to 10 lobes, or from 6 to 8 lobes as desired. In certain instances, the plurality of first lobes 116 may have more lobes than the plurality of second lobes 126, while in other instances, the plurality of first lobes 116 may have the same number of lobes or less lobes than the plurality of second lobes 126.

Figure 4:
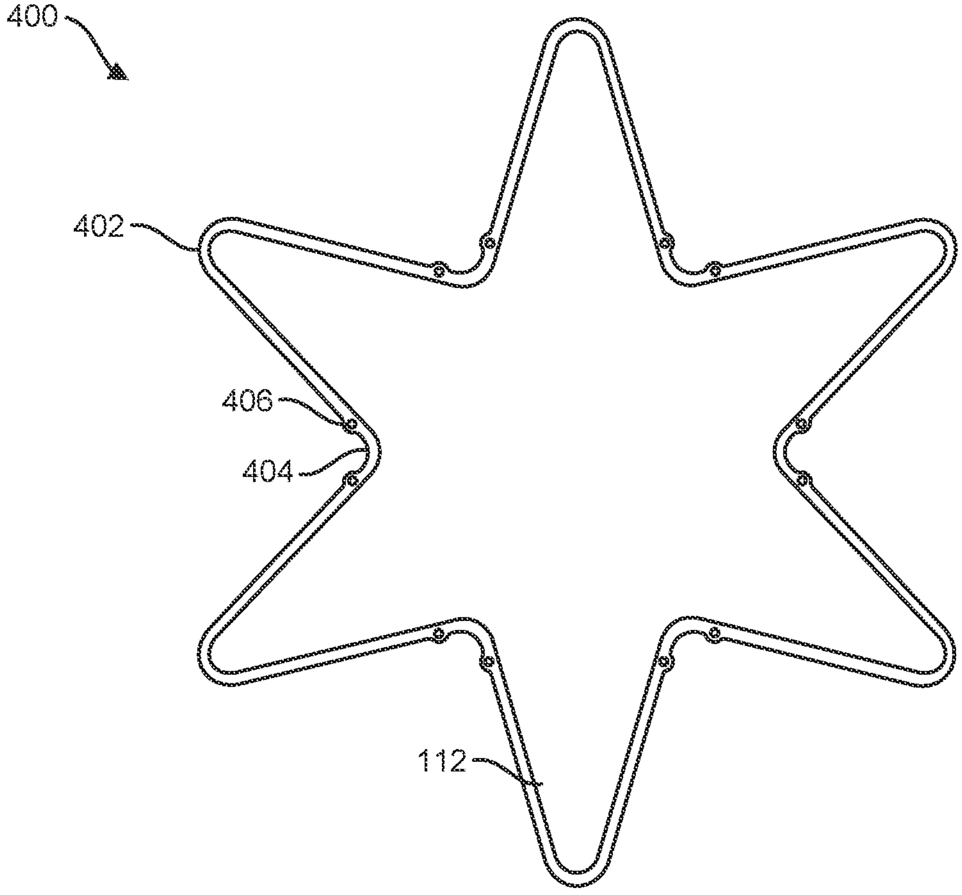
FIG. 4 shows an example frame component that may be used in an implantable medical device for regulating blood pressure in accordance with an embodiment.

FIG. 4 shows an example frame component 400 that may be used in an implantable medical device for regulating blood pressure in accordance with an embodiment. The frame component 400 may be used in place of one or both of the frame components 110, 120 shown and discussed above with reference to FIGS. 1-3. For example, the frame component 400 may take place of the first and/or second frame components 110, 120 maintain a lumen through a conduit portion 130. The frame component 400 may include elongate elements 112 that form the frame component 400. The elongate elements 112 may formed of a wire, cut-tube, or cut-sheet, for example. In certain instances, the elongate elements 112 may be attached to one another via a membrane (not shown). In addition and as discussed in detail above, the membrane such as an expanded polytetrafluoroethylene (ePTFE) membrane, may connect frame components 400 and form the conduit portion 130.

The membrane may span gaps between the elongate elements 112, and, in certain instances, may be arranged on at least a tissue engaging side of the frame component 400. In these instances, the membrane is configured to lessens frame erosion potential of the frame component 400. The elongate elements 112 may conform to the tissue surfaces surrounding the septum. In addition, the elongate elements 112 may lay flat against the tissue surfaces.

In certain instances, the elongate elements 112 form a star shape as is shown in FIG. 4. The star-shaped frame component 400 includes outer apices 402 and inner apices 404. In certain instances, the frame element 400 may include one or more eyelets 406 arranged with at least one of the outer apices 402 and the inner apices 404. The one or more eyelets 406 may be arranged on either side of the inner apices 404. In certain instances, each of the inner apices 404 include a pair of eyelets 406 as is shown in FIG. 4. In other instances, the eyelets 406 may alternatively be arranged with the outer apices 402. In yet other instances, the eyelets 406 may be arranged with the outer apices 402 and the inner apices 404. The eyelets 406 may be configured to interface with a delivery system to facilitate deployment of the frame element.

Figure 5:
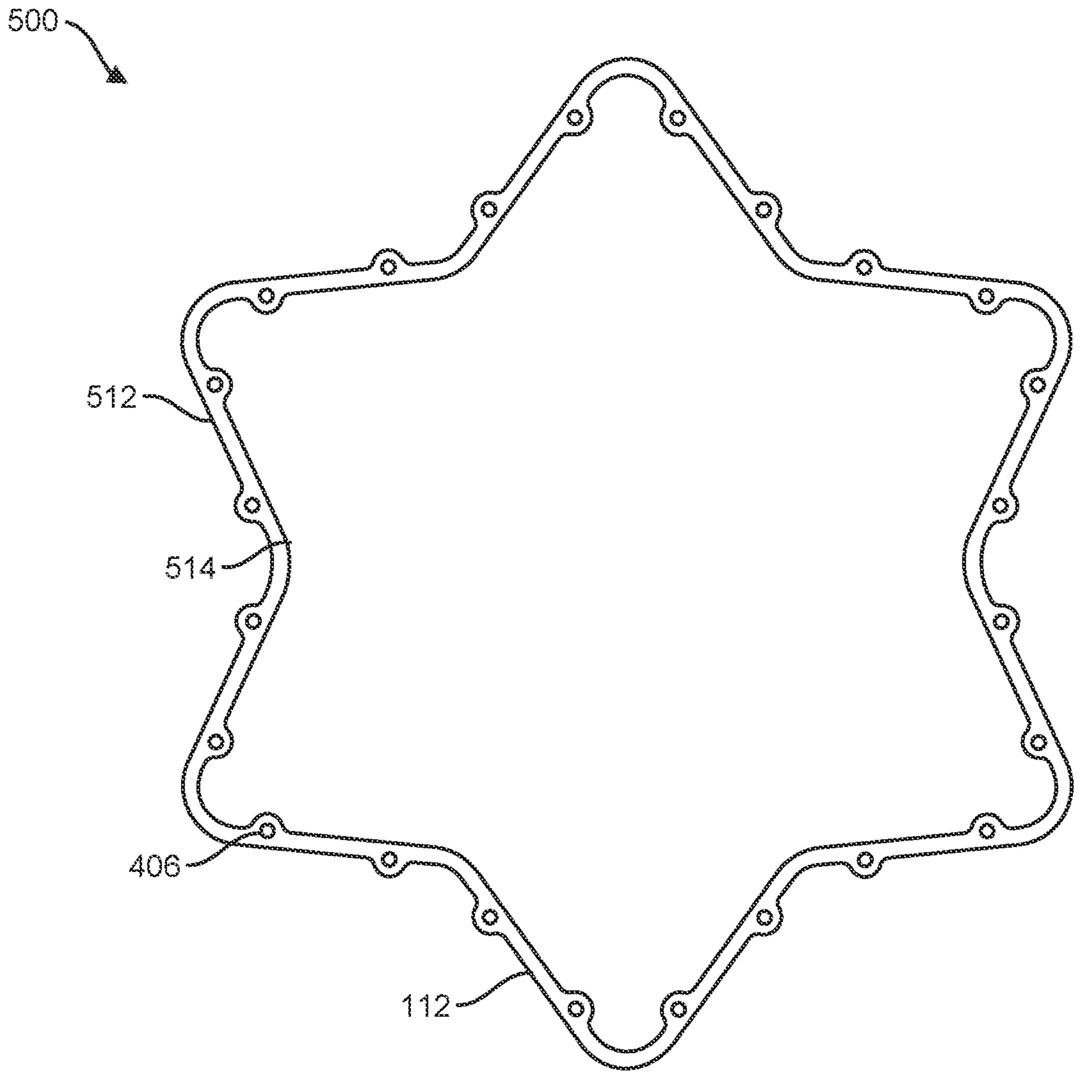
FIG. 5 shows another example frame component that may be used in an implantable medical device for regulating blood pressure in accordance with an embodiment.

FIG. 5 shows another example frame component that may be used in an implantable medical device for regulating blood pressure in accordance with an embodiment. The frame component 500 may be used in place of one or both of the frame components 110, 120 shown and discussed above with reference to FIGS. 1-3. For example, the frame component 500 may take place of the first and/or second frame components 110, 120 maintain a lumen through a conduit portion 130. The frame component 500 may include elongate elements 112 that form the frame component 500. The elongate elements 112 may formed of a wire, cut-tube, or cut-sheet, for example. In certain instances, the elongate elements 112 may be attached to one another via a membrane (not shown). In addition and as discussed in detail above, the membrane such as an expanded polytetrafluoroethylene (ePTFE) membrane, may connect frame components 500 and form the conduit portion 130.

The membrane may span gaps between the elongate elements 112, and, in certain instances, may be arranged on at least a tissue engaging side of the frame component 500. In these instances, the membrane is configured to lessens frame erosion potential of the frame component 400. The elongate elements 112 may conform to the tissue surfaces surrounding the septum. In addition, the elongate elements 112 may lay flat against the tissue surfaces.

In certain instances, the elongate elements 112 form a star shape as is shown in FIG. 5. The star-shaped frame element 500 includes a first surface 512 and a second surface 514. In certain instances, the frame component 500 may include eyelets 406 extending about the frame component 500. The eyelets 406 may be arranged along one or both of the first surface 512 and the second surface 514. In certain instances, the eyelets 406 extend about the frame component 500 and are arranged alternatively on the first surface 512 and the second surface 514 as is shown in FIG. 5. The eyelets 406 may be configured to interface with a delivery system to facilitate deployment of the frame element.

Figure 6:
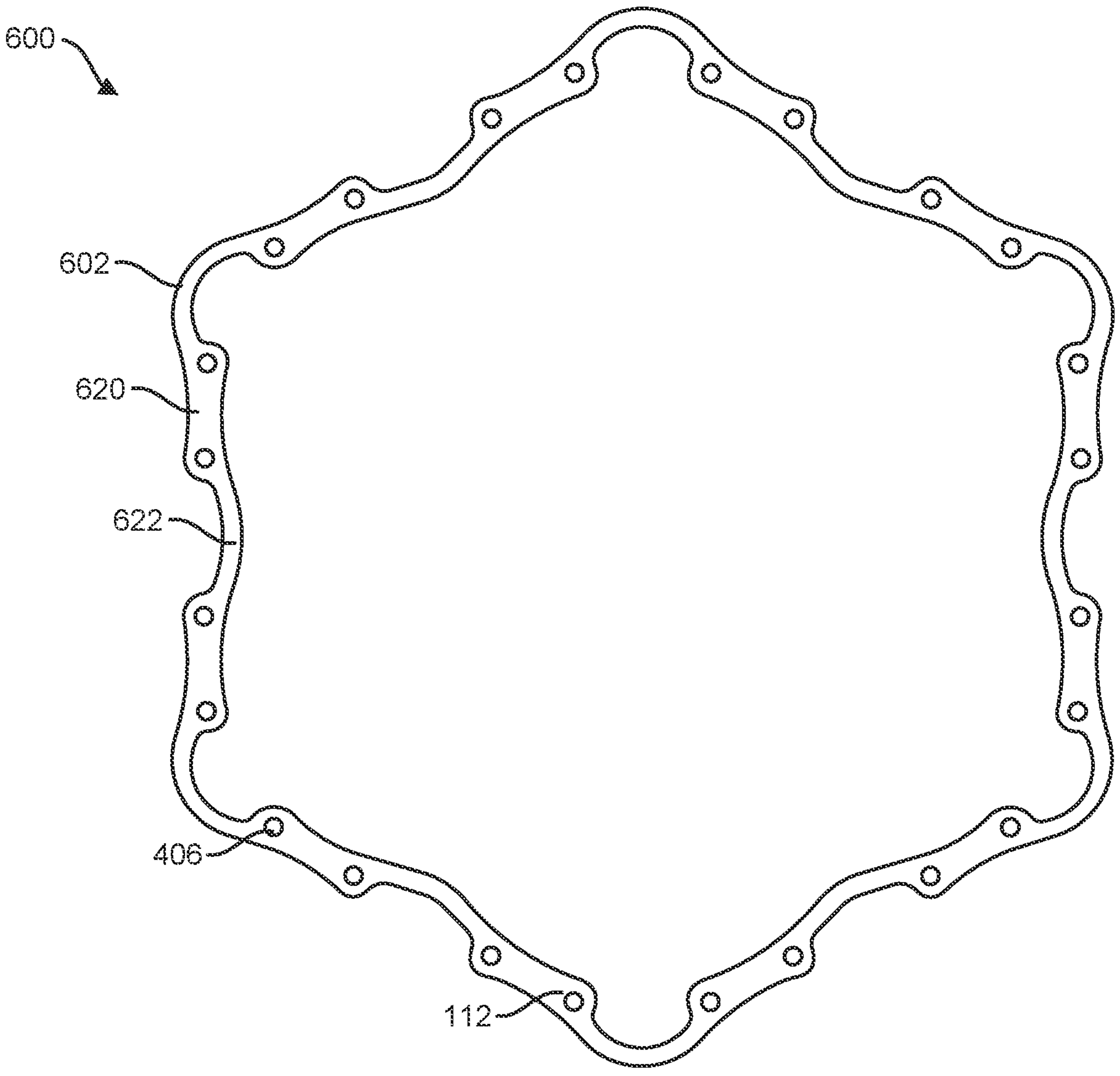
FIG. 6 shows an example frame component that may be used in an implantable medical device for regulating blood pressure in accordance with an embodiment.

FIG. 6 shows an example frame component that may be used in an implantable medical device for regulating blood pressure in accordance with an embodiment. The frame component 600 may be used in place of one or both of the frame components 110, 120 shown and discussed above with reference to FIGS. 1-3. For example, the frame component 600 may take place of the first and/or second frame components 110, 120 maintain a lumen through a conduit portion 130. The frame component 600 may include elongate elements 112 that form the frame component 600. The elongate elements 112 may formed of a wire, cut-tube, or cut-sheet, for example. In certain instances, the elongate elements 112 may be attached to one another via a membrane (not shown). In addition and as discussed in detail above, the membrane such as an expanded polytetrafluoroethylene (ePTFE) membrane, may connect frame components 600 and form the conduit portion 130.

The membrane may span gaps between the elongate elements 112, and, in certain instances, may be arranged on at least a tissue engaging side of the frame component 600. In these instances, the membrane is configured to lessens frame erosion potential of the frame component 600. The elongate elements 112 may conform to the tissue surfaces surrounding the septum. In addition, the elongate elements 112 may lay flat against the tissue surfaces.

In certain instances, the elongate elements 112 include variable width portions as is shown in FIG. 6. The frame component 600 includes apices 602 arranged about the frame element 600. Between the apices 602, the elongate elements 112 may vary in width. The frame element 600 may include greater width portions 620 and less width portions 622. In certain instances, the frame element 600 may include two greater width portions 620 and one lesser width portion 622 in between two apices 602. In certain instances, the lesser width portion 622 is between the two greater width portions 620. In addition, the frame element 600 may also include eyelets 406. In certain instances, the eyelets 406 are arranged with the greater width portions 620 of the frame element 600. The eyelets 406 may be configured to interface with a delivery system to facilitate deployment of the frame element.

Figure 7:
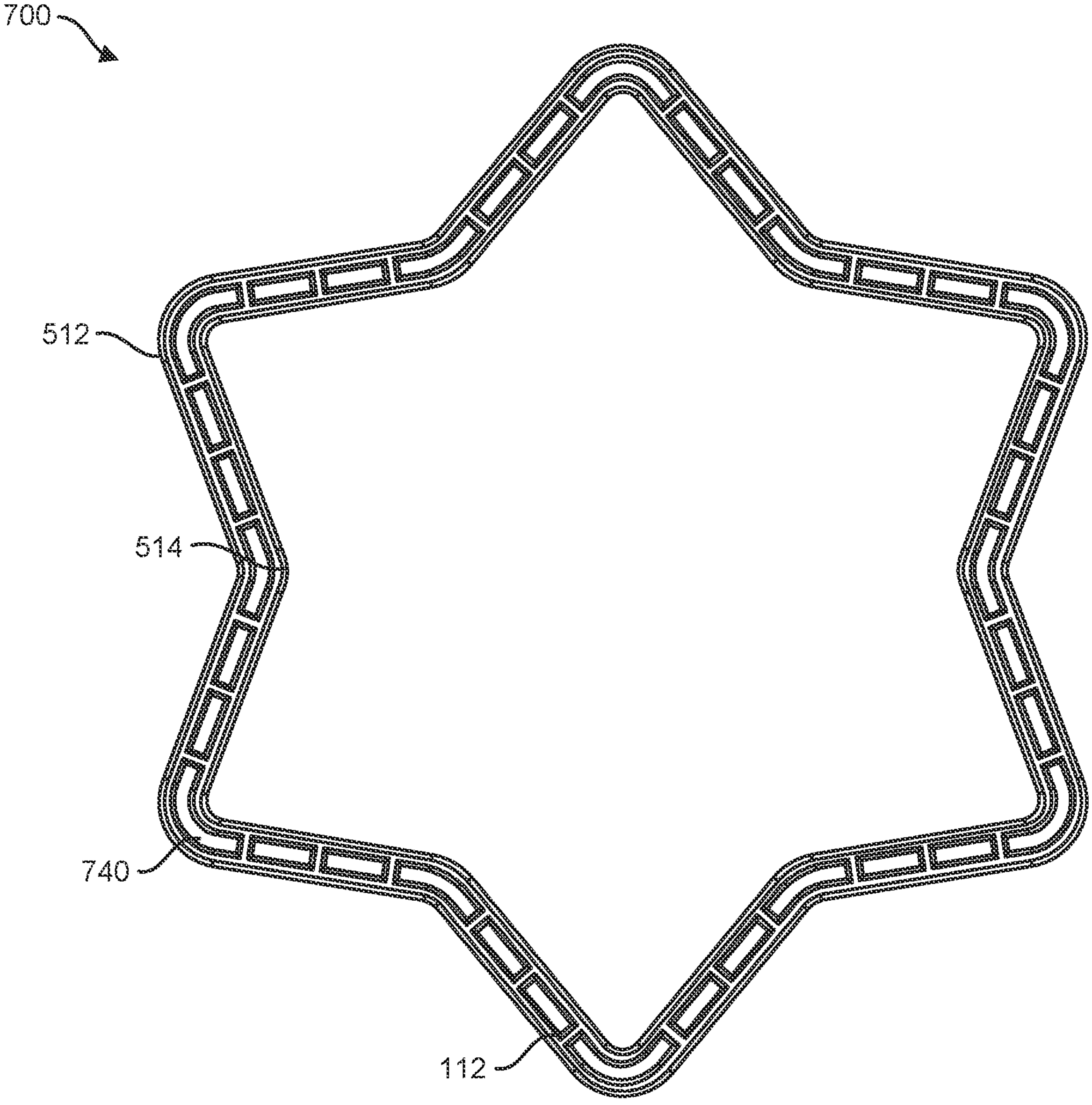
FIG. 7 shows an example frame component that may be used in an implantable medical device for regulating blood pressure in accordance with an embodiment.

FIG. 7 shows an example frame component that may be used in an implantable medical device for regulating blood pressure in accordance with an embodiment. The frame component 700 may be used in place of one or both of the frame components 110, 120 shown and discussed above with reference to FIGS. 1-3. For example, the frame component 700 may take place of the first and/or second frame components 110, 120 maintain a lumen through a conduit portion 130. The frame component 700 may include elongate elements 112 that form the frame component 700. The elongate elements 112 may formed of a wire, cut-tube, or cut-sheet, for example. In certain instances, the elongate elements 112 may be attached to one another via a membrane (not shown). In addition and as discussed in detail above, the membrane such as an expanded polytetrafluoroethylene (ePTFE) membrane, may connect frame components 700 and form the conduit portion 130.

The membrane may span gaps between the elongate elements 112, and, in certain instances, may be arranged on at least a tissue engaging side of the frame component 700. In these instances, the membrane is configured to lessens frame erosion potential of the frame component 700. The elongate elements 112 may conform to the tissue surfaces surrounding the septum. In addition, the elongate elements 112 may lay flat against the tissue surfaces.

Figure 8:
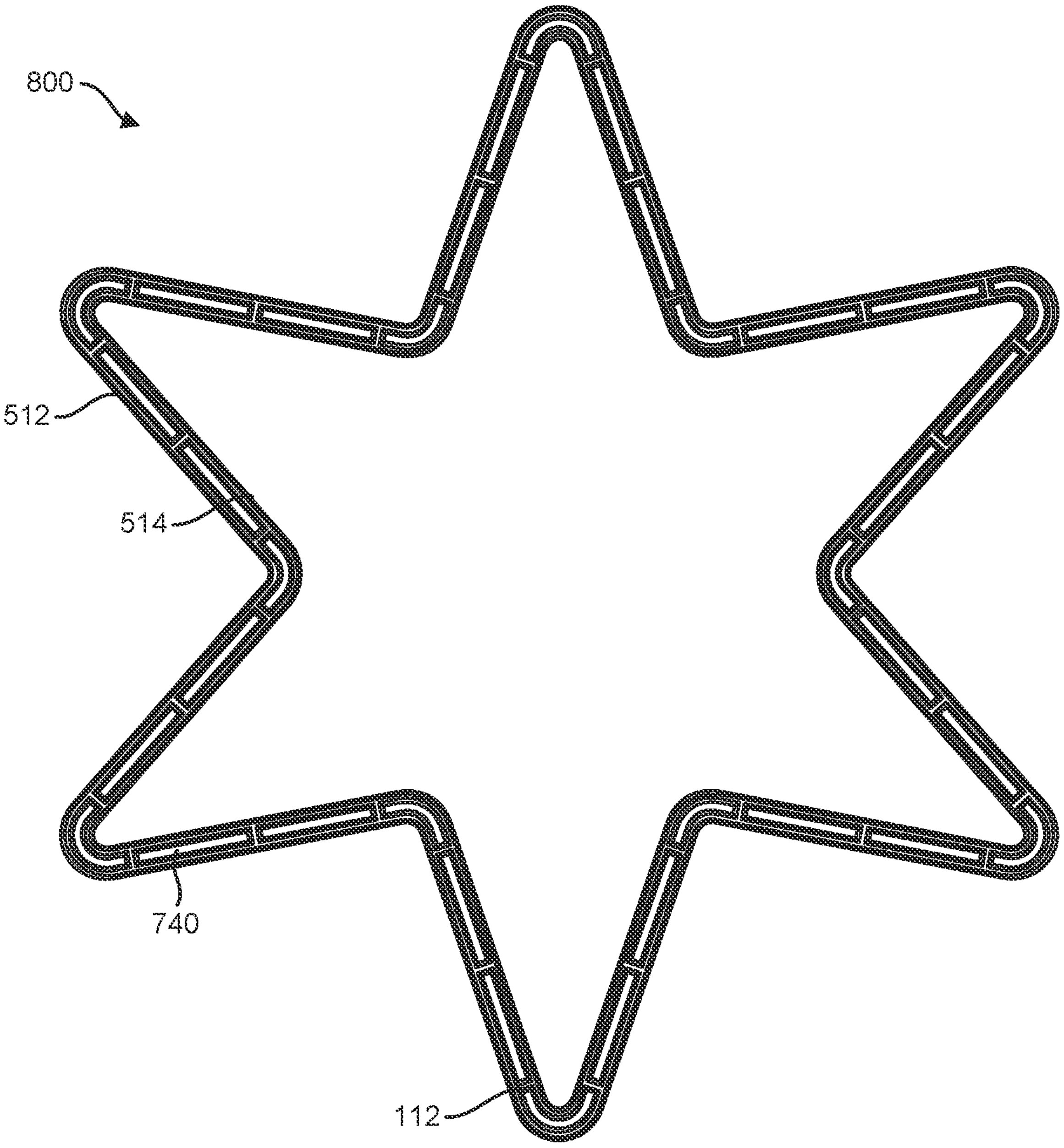
FIG. 8 shows an example frame component that may be used in an implantable medical device for regulating blood pressure in accordance with an embodiment.

In certain instances, the elongate elements 112 form a star shape as is shown in FIG. 7. The star-shaped frame element 700 includes a first surface 512 and a second surface 514. In certain instances, the frame element 700 may include openings 740 extending about the frame element 700 between the first surface 512 and the second surface 514. In certain instances, the openings 740 may be rectangular in shape. The openings 740 may be configured to interface with a delivery system to facilitate deployment of the frame element. FIG. 8 shows another example frame component 800 having openings 740 between the first surface 512 and the second surface 514.

Figure 9:
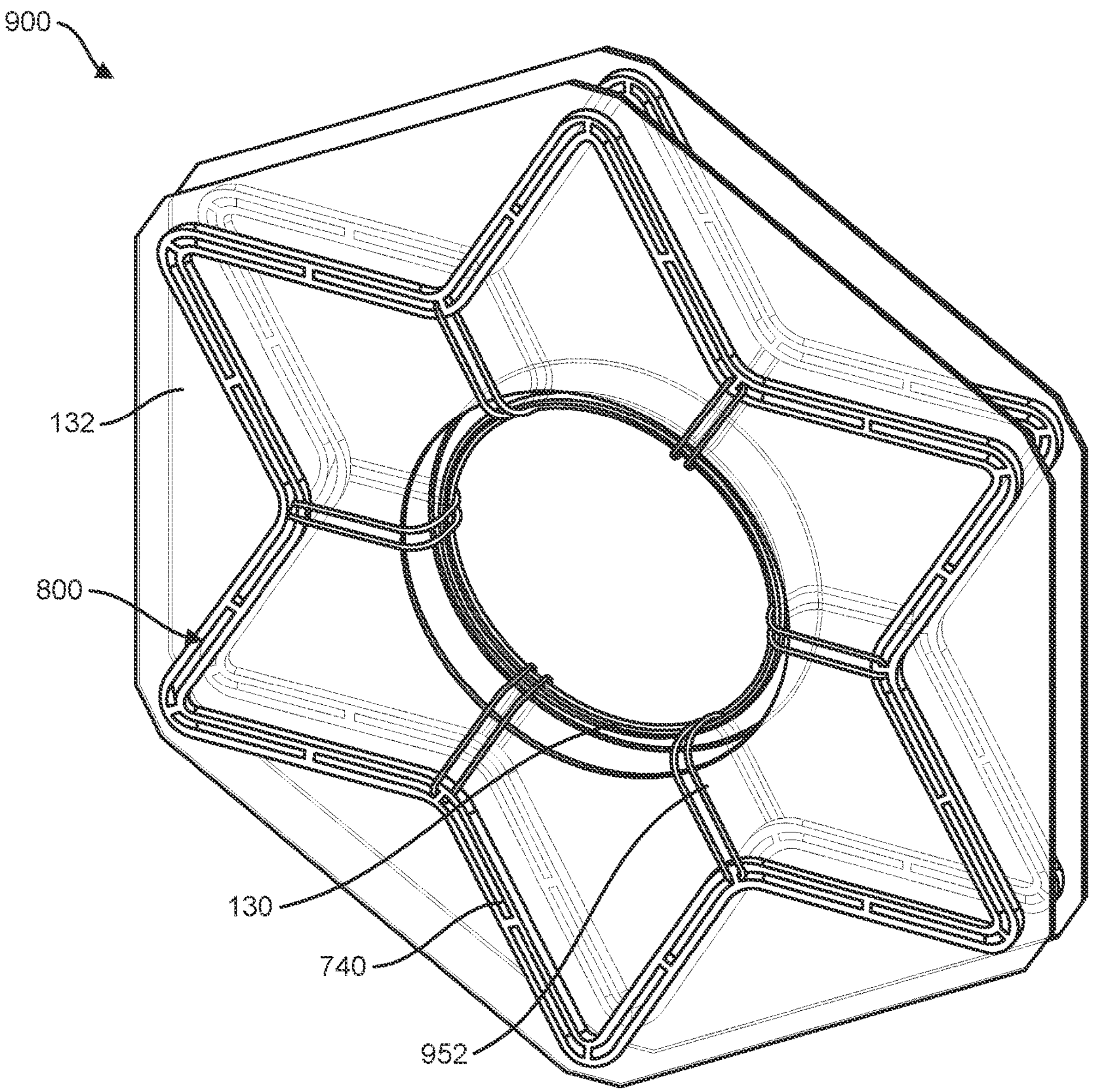
FIG. 9 shows an example implantable medical device for regulating blood pressure in accordance with an embodiment.

FIG. 9 shows an example implantable medical device 900 for regulating blood pressure in accordance with an embodiment. The device 900 includes two of the frame components 800, as discussed above relative to FIGS. 7-8, and a membrane 132 connecting the components 800. As shown in FIG. 9, the device 900 includes a conduit portion 130 as discussed in detail above. The frame components 800 may be any one of the frame components discussed herein.

Figure 10B:
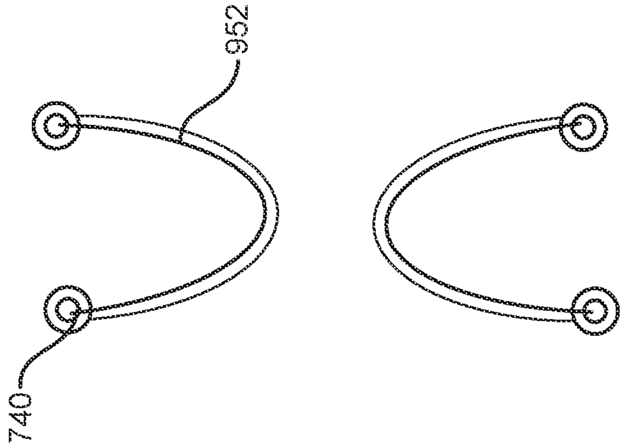
FIG. 10B shows an example suture arrangement, that may be used with the implantable medical device shown in FIG. 10A, in accordance with an embodiment.
Figure 10A:
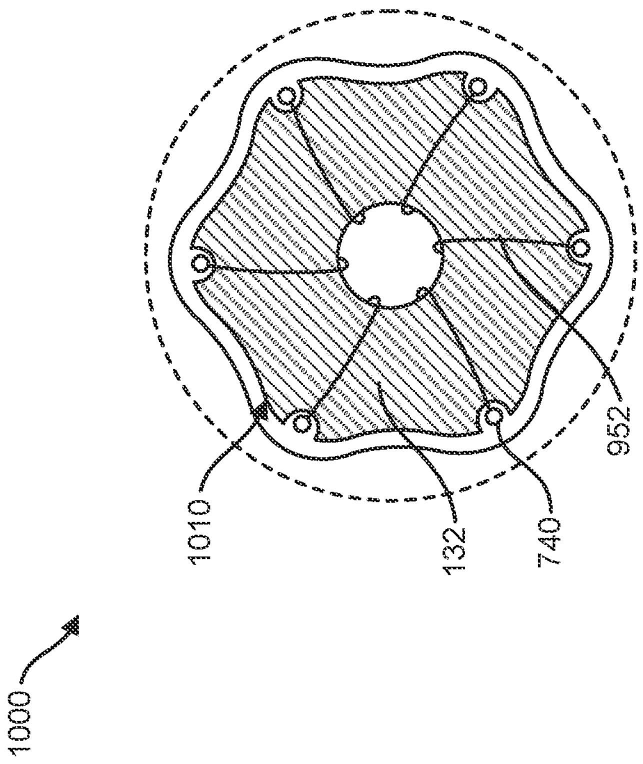
FIG. 10A shows an end view of an example implantable medical device for regulating blood pressure in accordance with an embodiment.

As shown, the device 900 includes one or more tethers 952 connecting the frame components 800 and arranged through the conduit portion 130. In certain instances, the one or more tethers 952 are arranged through the openings 740 in the frame components 800. The tethers 952 may be configured to structurally enhance the conduit portion 130. FIG. 10A shows an end view of another an example implantable medical device 1000 and frame component 1010 for regulating blood pressure in having tethers 952 arranged through openings 740 spaced about an inner perimeter of the frame component 1010. The tethers 952 may be fibers, wire, polymer (e.g., ePTFE) strips, braided fibers or wires, interwoven fibers or wires, or other similar structural components. FIG. 10B shows an example tether 952 arrangement, that may be used with the implantable medical device shown in FIG. 10A, in accordance with an embodiment.

Figure 11:
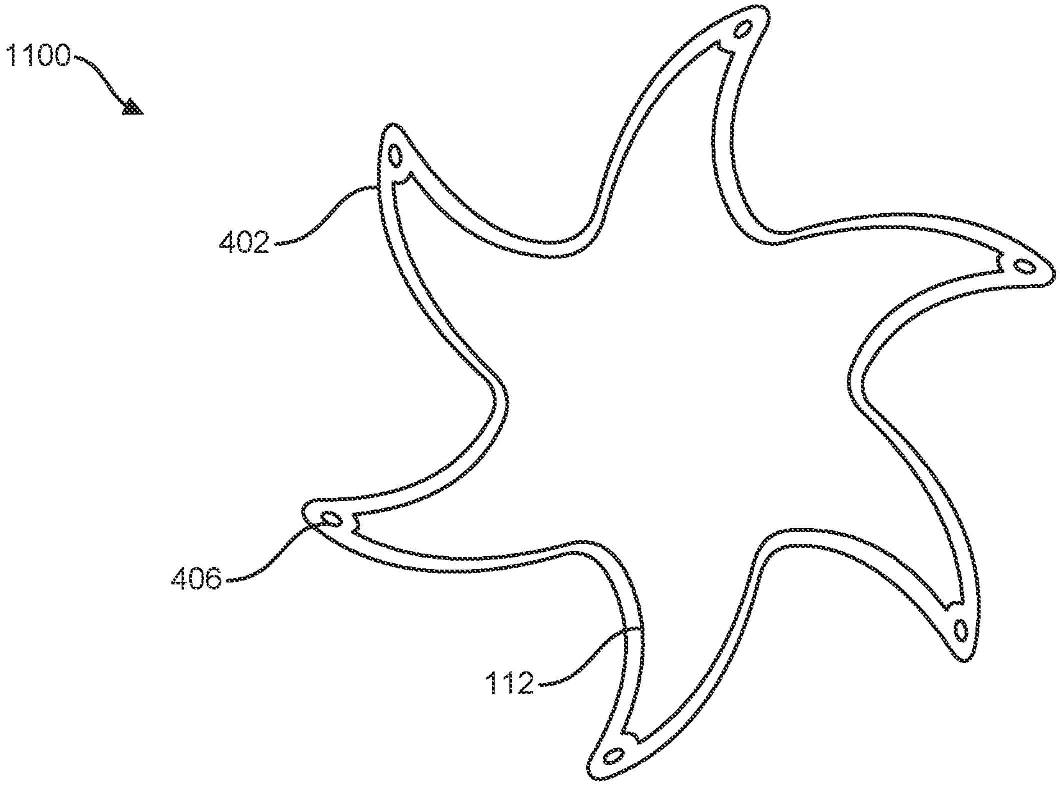
FIG. 11 shows another example frame component that may be used in an implantable medical device for regulating blood pressure in accordance with an embodiment.

FIG. 11 shows another example frame component that may be used in an implantable medical device for regulating blood pressure in accordance with an embodiment. The frame component 1100 may be used in place of one or both of the frame components 110, 120 shown and discussed above with reference to FIGS. 1-3. For example, the frame component 1100 may take place of the first and/or second frame components 110, 120 maintain a lumen through a conduit portion 130. The frame component 1100 may include elongate elements 112 that form the frame component 1100. The elongate elements 112 may formed of a wire, cut-tube, or cut-sheet, for example. In certain instances, the elongate elements 112 may be attached to one another via a membrane (not shown). In addition and as discussed in detail above, the membrane such as an expanded polytetrafluoroethylene (ePTFE) membrane, may connect frame components 1100 and form the conduit portion 130.

The membrane may span gaps between the elongate elements 112, and, in certain instances, may be arranged on at least a tissue engaging side of the frame component 1100. In these instances, the membrane is configured to lessens frame erosion potential of the frame component 1100. The elongate elements 112 may conform to the tissue surfaces surrounding the septum. In addition, the elongate elements 112 may lay flat against the tissue surfaces.

In certain instances, the elongate elements 112 form a curved star shape as is shown in FIG. 11. The star-shaped frame element 1100 includes elongate elements 112 include curvatures between apices 402. In certain instances, the frame component 1100 also includes eyelets 406 arranged with each of the apices 402. The eyelets 406 may be configured to interface with a delivery system to facilitate deployment of the frame element.

Figure 12:
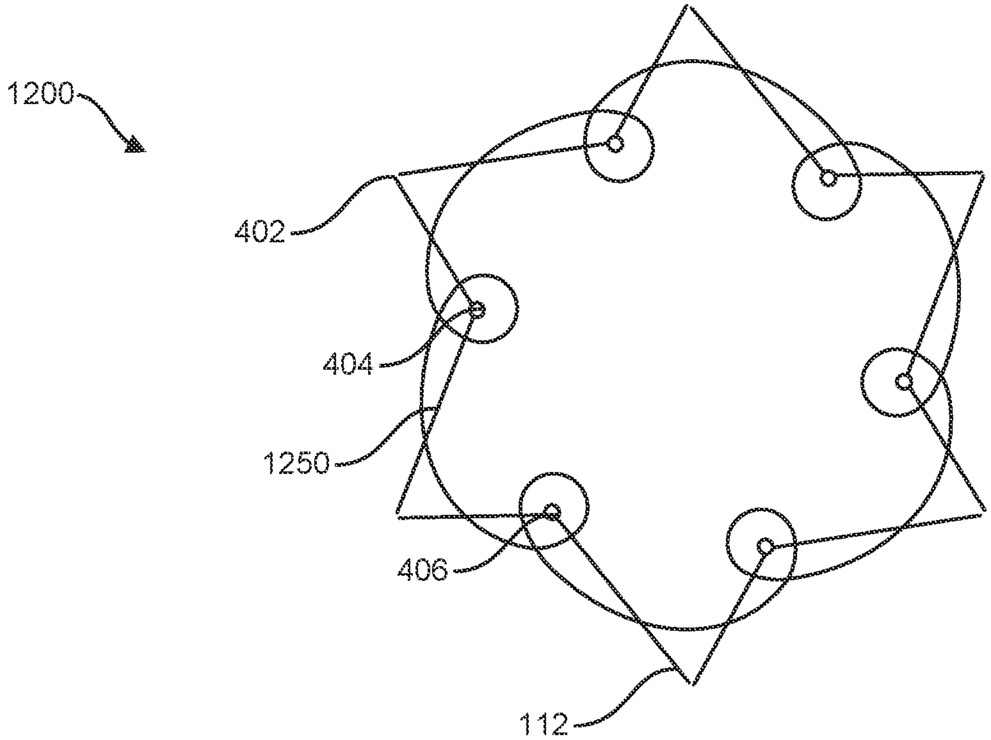
FIG. 12 shows another example frame component that may be used in an implantable medical device for regulating blood pressure in accordance with an embodiment.

FIG. 12 shows another example frame component that may be used in an implantable medical device for regulating blood pressure in accordance with an embodiment. The frame component 1200 may be used in place of one or both of the frame components 110, 120 shown and discussed above with reference to FIGS. 1-3. For example, the frame component 1200 may take place of the first and/or second frame components 110, 120 maintain a lumen through a conduit portion 130. The frame component 1200 may include elongate elements 112 that form the frame component 1200. The elongate elements 112 may formed of a wire, cut-tube, or cut-sheet, for example. In certain instances, the elongate elements 112 may be attached to one another via a membrane (not shown). In addition and as discussed in detail above, the membrane such as an expanded polytetrafluoroethylene (ePTFE) membrane, may connect frame components 1200 and form the conduit portion 130.

The membrane may span gaps between the elongate elements 112, and, in certain instances, may be arranged on at least a tissue engaging side of the frame component 1200. In these instances, the membrane is configured to lessens frame erosion potential of the frame component 1200. The elongate elements 112 may conform to the tissue surfaces surrounding the septum. In addition, the elongate elements 112 may lay flat against the tissue surfaces.

In certain instances, the elongate elements 112 form a star shape as is shown in FIG. 12. The star-shaped frame element 1200 includes outer apices 402 and inner apices 404. In certain instances, the frame element 1200 may include eyelets 406 arranged with at least one of the outer apices 402 and the inner apices 404. The eyelets 406 may be arranged on the inner apices 404. In certain instances, a tether 1250 is arranged through and connects each of the eyelets 406. The tether 1250 may structurally enhance the frame element 1200.

Figure 13A:
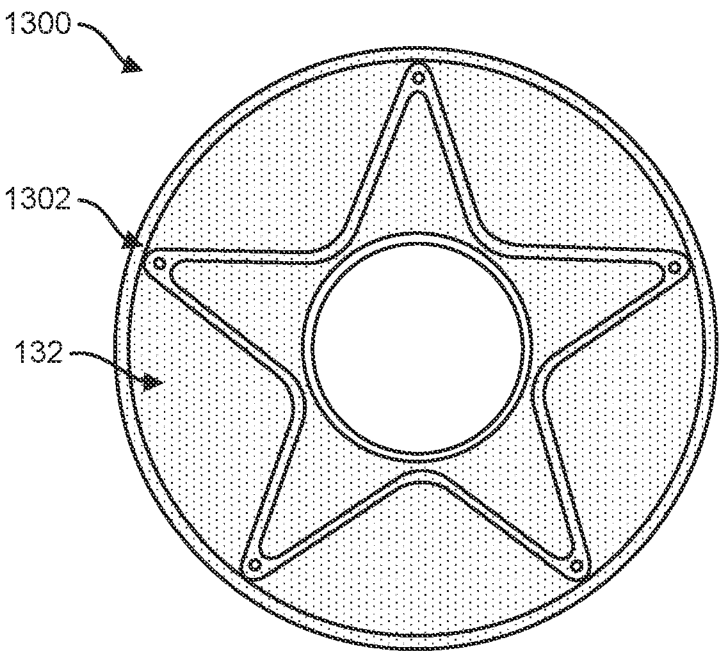
FIG. 13A shows an end view of an example implantable medical device for regulating blood pressure in accordance with an embodiment.
Figure 13B:
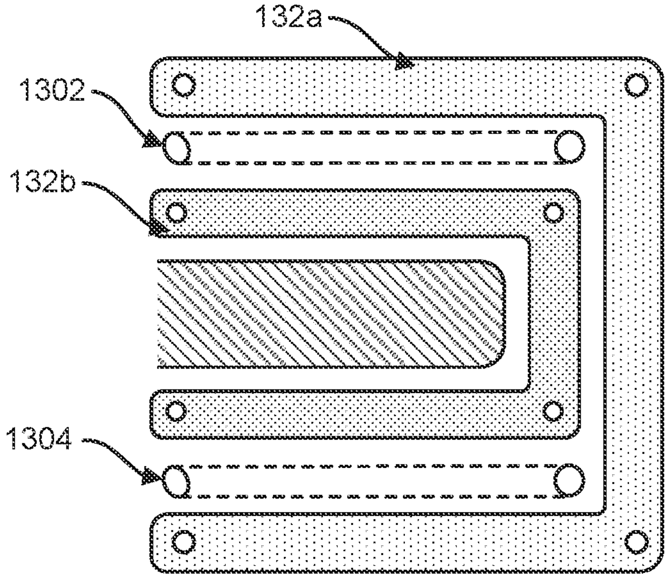
FIG. 13B shows an example material arrangement be used with the implantable medical device shown in FIG. 13A in accordance with an embodiment.

FIG. 13A shows an end view of an example implantable medical device 1300 for regulating blood pressure in accordance with an embodiment. FIG. 13B shows an example material arrangement be used with the implantable medical device 1300 shown in FIG. 13A in accordance with an embodiment. As shown in FIGS. 13A-B, the implantable medical device 1300 includes frame components 1302, 1304 and a membrane 132. The membrane 132 may include two layers 132*a*, 132*b* as shown in FIG. 13B. In certain instances, the two layers 132*a*, 132*b* of the membrane 132 sandwich the frame components 1302, 1304. The two layers 132*a*, 132*b* of the membrane 132 may have different material properties and may facilitate flexibility along different portions of the device 1300.

Figure 14:
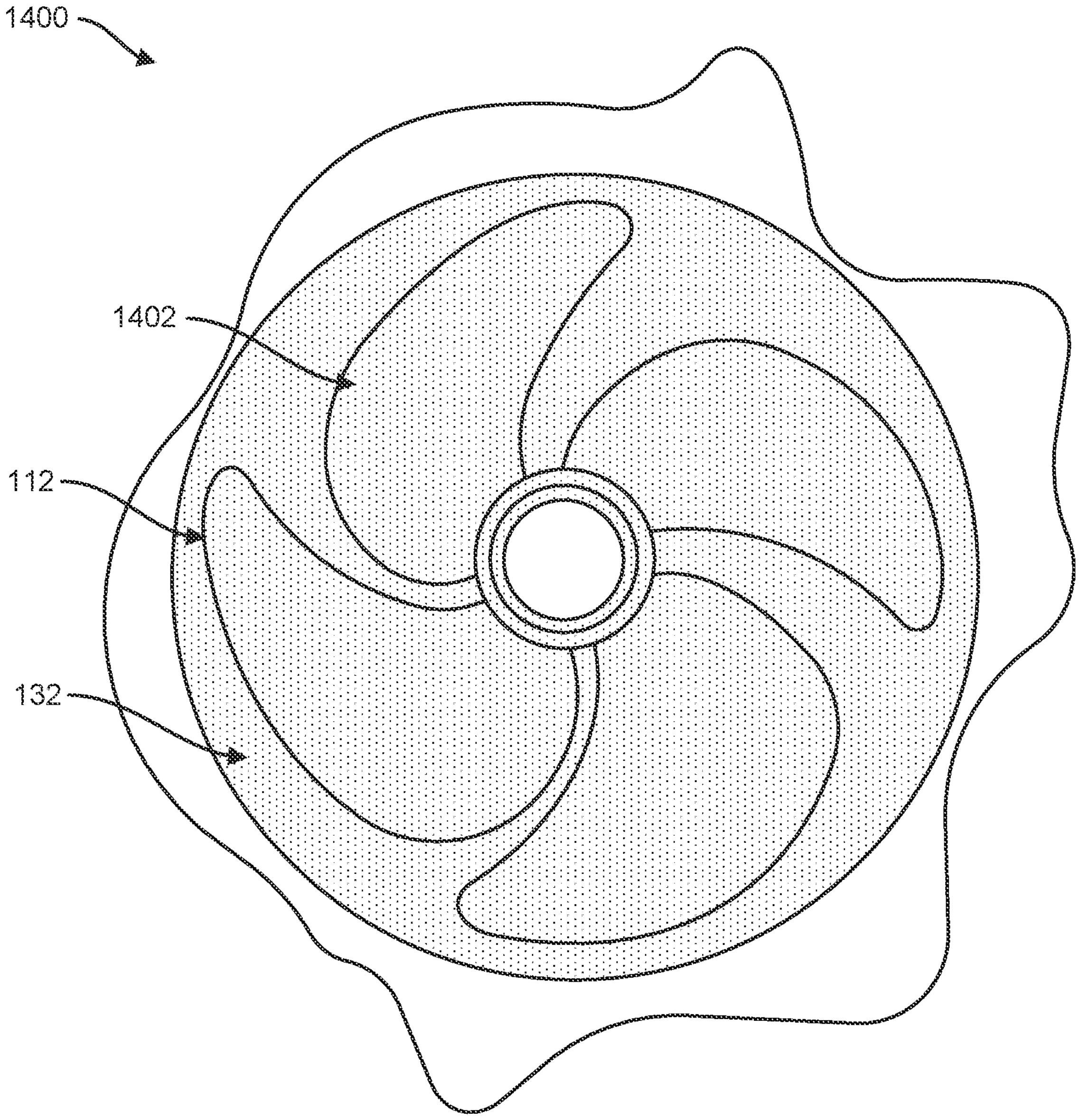
FIG. 14 shows an end view of an example implantable medical device for regulating blood pressure in accordance with an embodiment.

FIG. 14 shows an end view of an example implantable medical device 1400 for regulating blood pressure in accordance with an embodiment. The device 1400 includes one or more frame components 1402 as discussed in detail above. As shown, the frame component 1402 includes a fan or starfish like shape with curved elongated elements 112. The frame component 1402 may retract and twist to deploy. The device includes a membrane 132 coupled or attached to the frame component 1602 as discussed in detail above.

Figure 15:
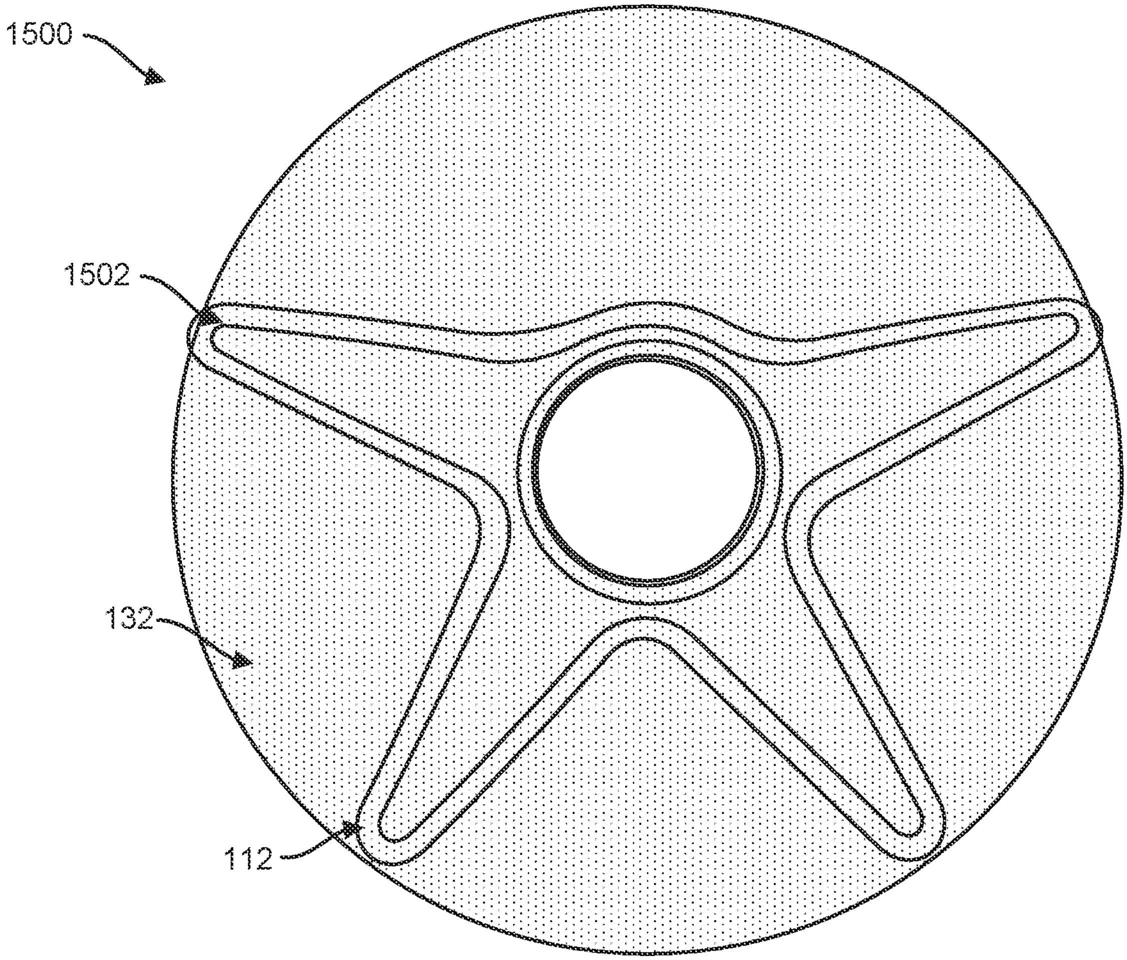
FIG. 15 shows an end view of an example implantable medical device for regulating blood pressure in accordance with an embodiment.

FIG. 15 shows an end view of an example implantable medical device 1500 for regulating blood pressure in accordance with an embodiment. The device 1500 includes one or more frame components 1502 as discussed in detail above. As shown, the frame component 1502 includes a partial star shape formed by elongated elements 112. In certain instances, the frame component 1502 may include less of the star-like branches that are formed by the elongated elements 112 than shown. The device includes a membrane 132 coupled or attached to the frame component 1502 as discussed in detail above.

Figure 16:
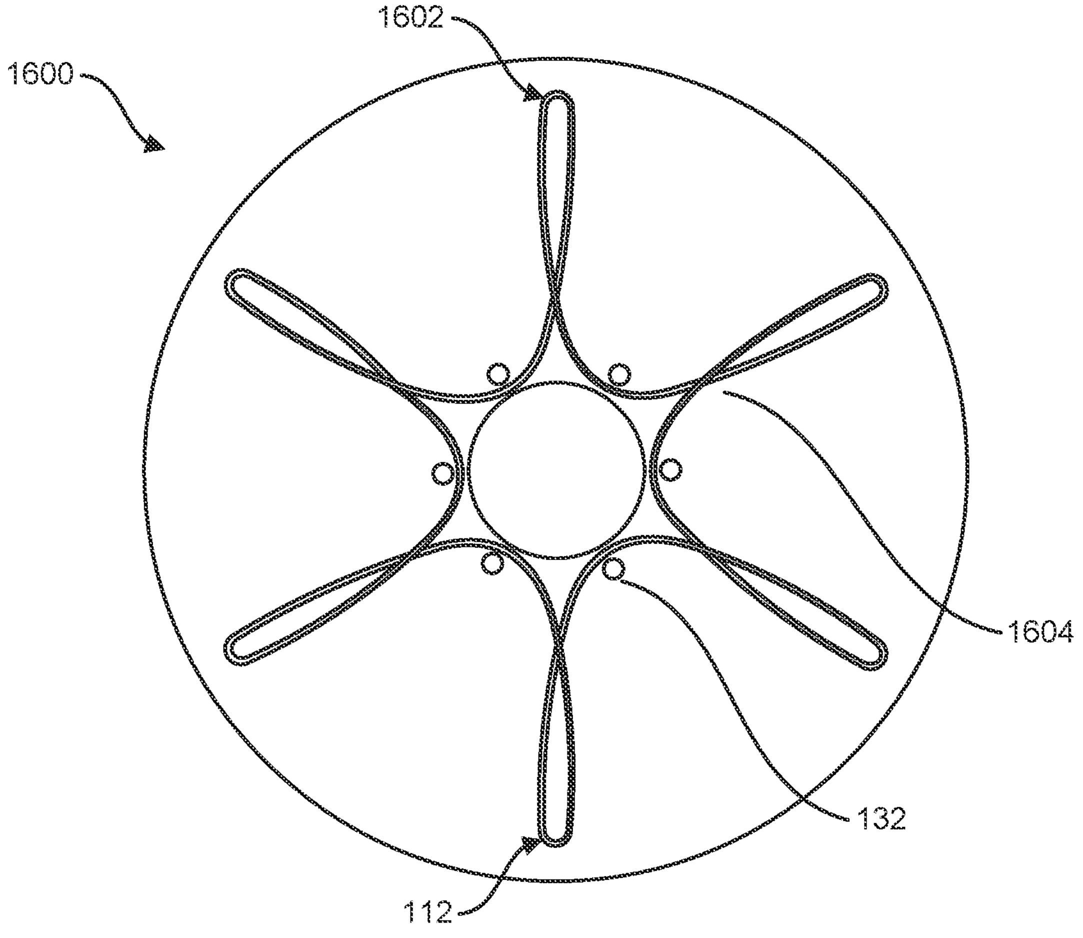
FIG. 16 shows an end view of an example implantable medical device for regulating blood pressure in accordance with an embodiment.

FIG. 16 shows an end view of an example implantable medical device 1600 for regulating blood pressure in accordance with an embodiment. The device 1600 includes one or more frame components 1602 as discussed in detail above. The device includes a membrane 132 coupled or attached to the frame component 1602 as also discussed in detail above. In certain instances, the frame component 1602 is formed by elongate elements 112 that include a plurality of loops 1604. The elongate elements 112 extend outwardly and overlap upon itself to form the loops 1604 as is shown.

Figure 17:
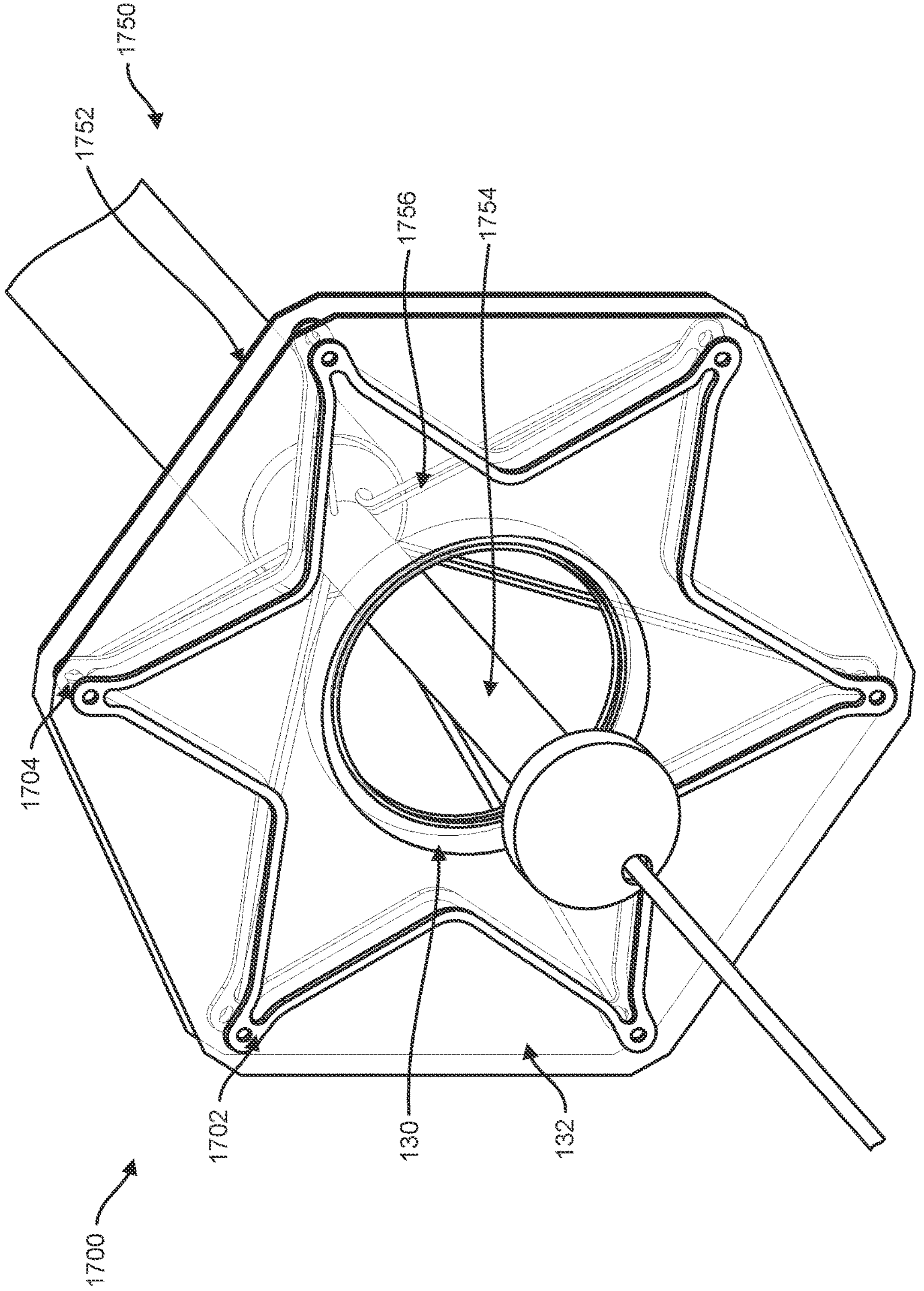
FIG. 17 shows an example implantable medical device for regulating blood pressure and example delivery system in accordance with an embodiment.
Figure 18:
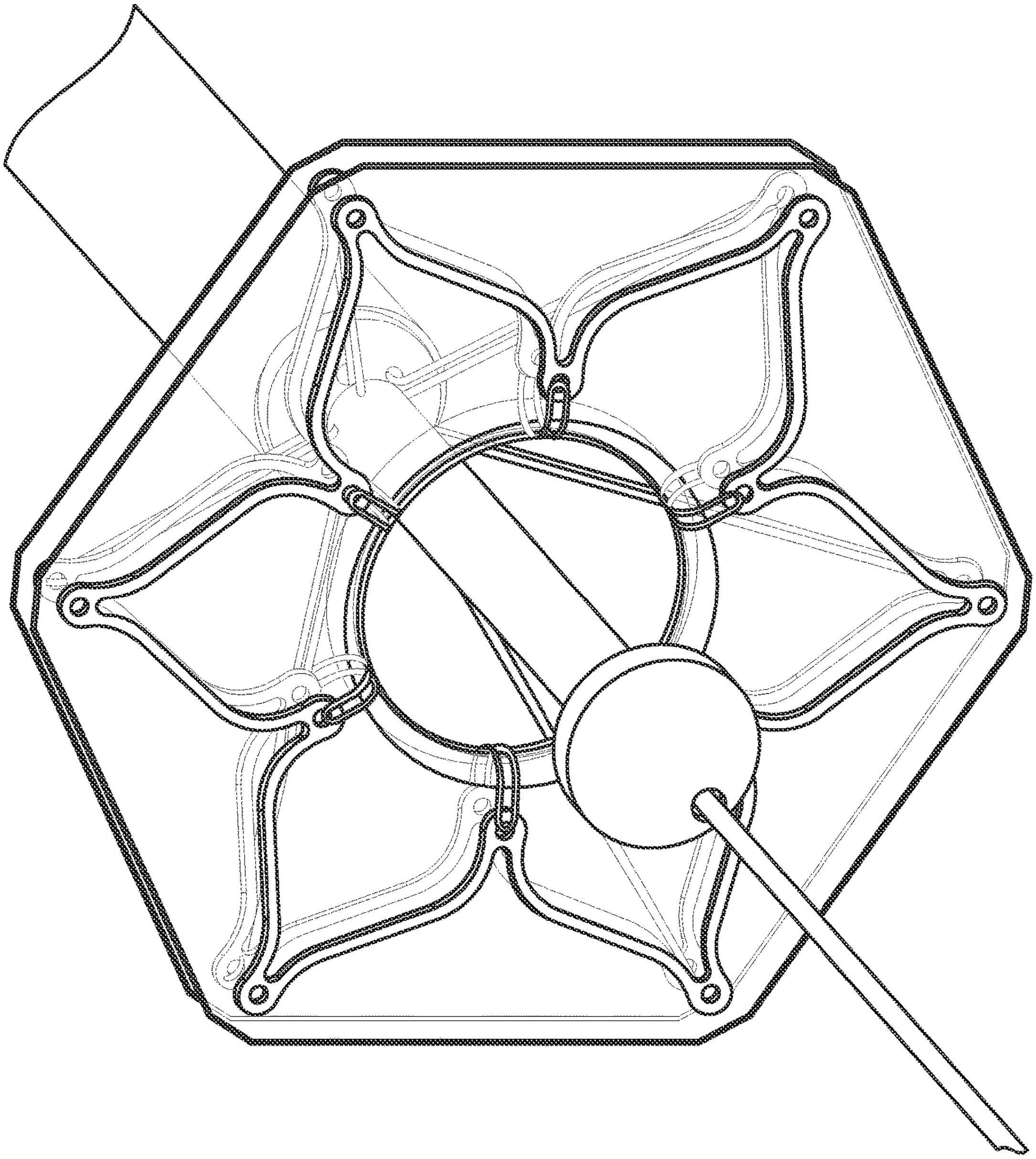
FIG. 18 shows another example implantable medical device for regulating blood pressure and example delivery system in accordance with an embodiment.
Figure 19:
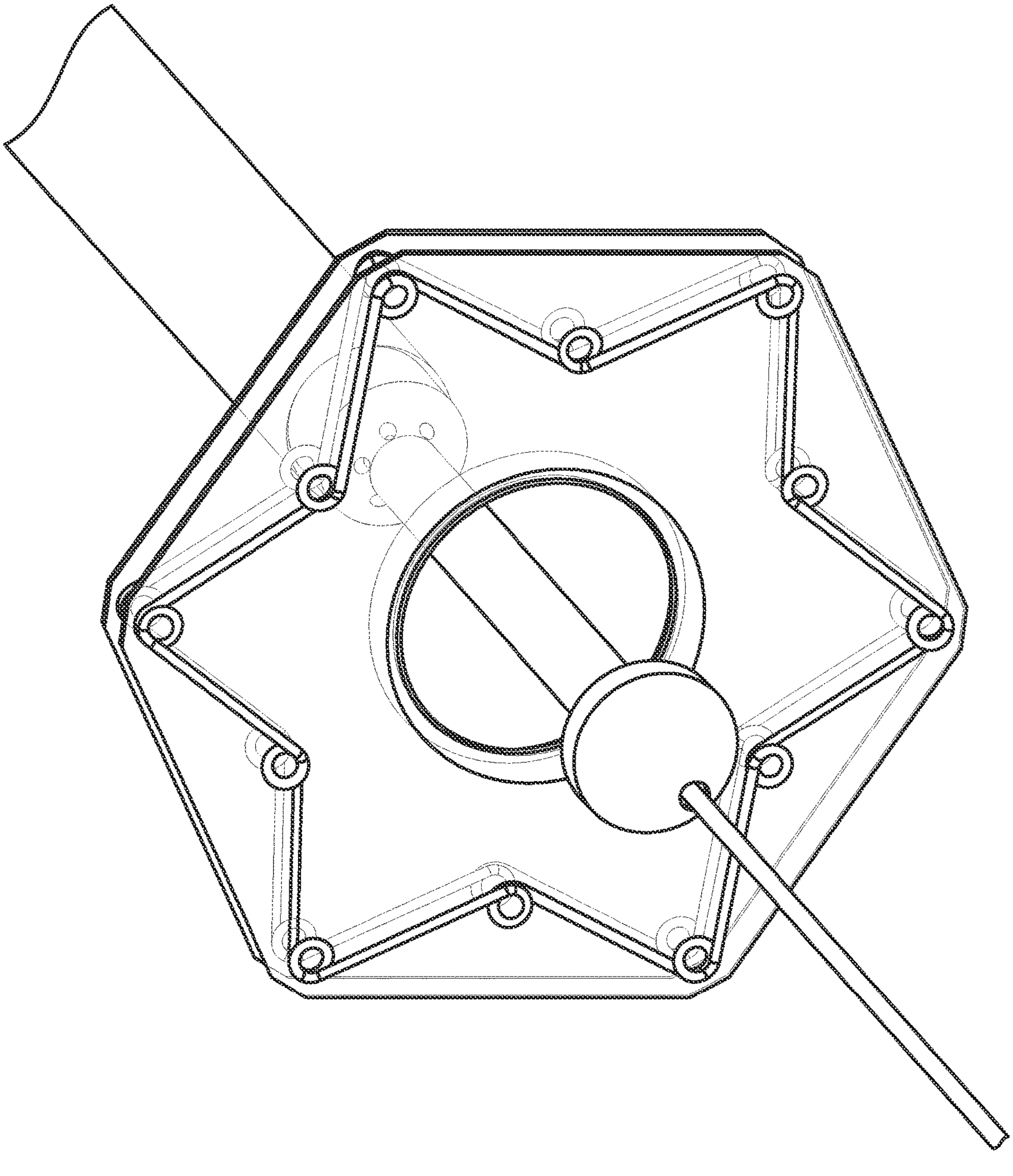
FIG. 19 shows an example implantable medical device for regulating blood pressure and example delivery system in accordance with an embodiment.
Figure 20:
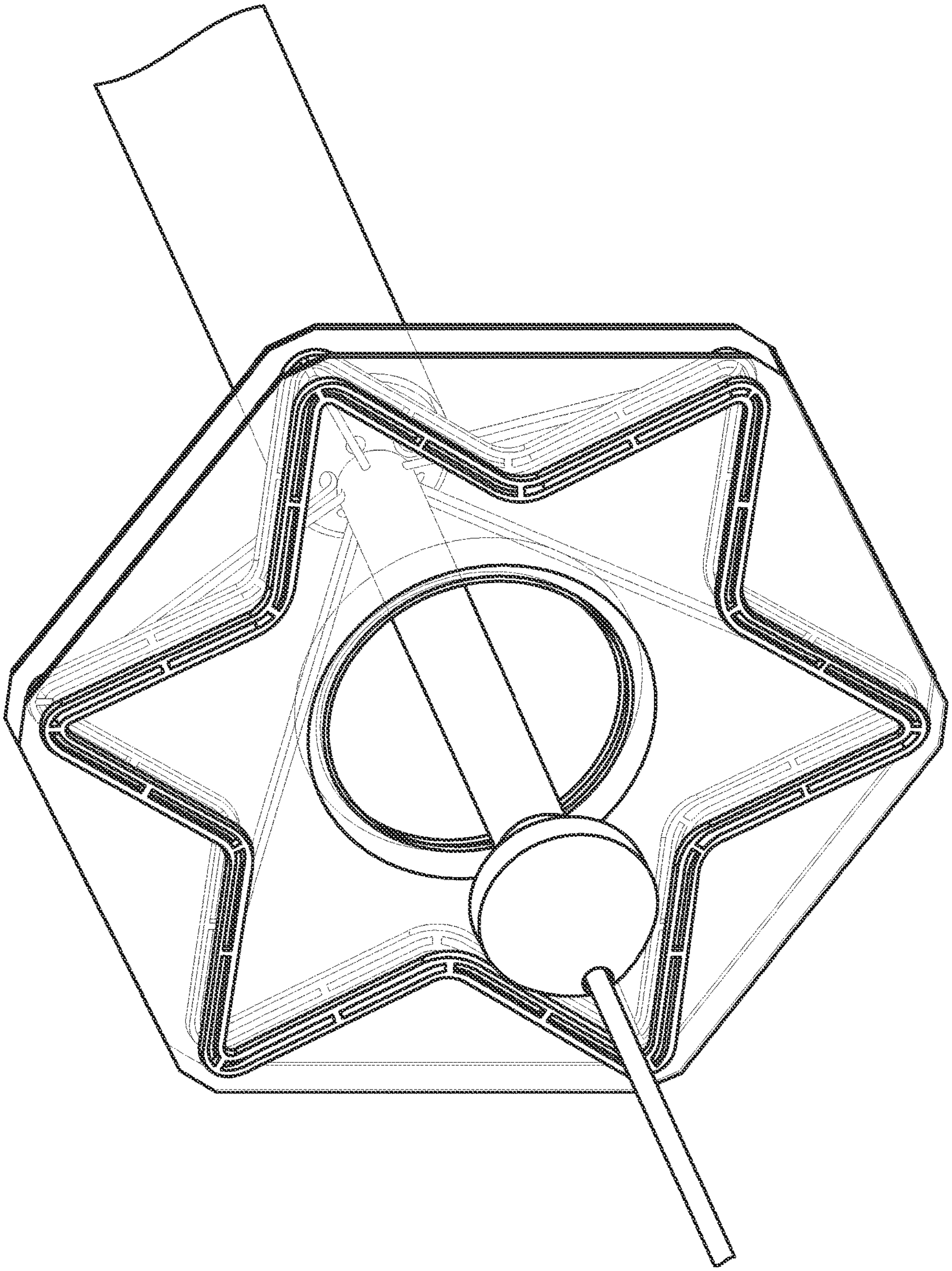
FIG. 20 shows an example implantable medical device for regulating blood pressure and example delivery system in accordance with an embodiment.
Figure 21:
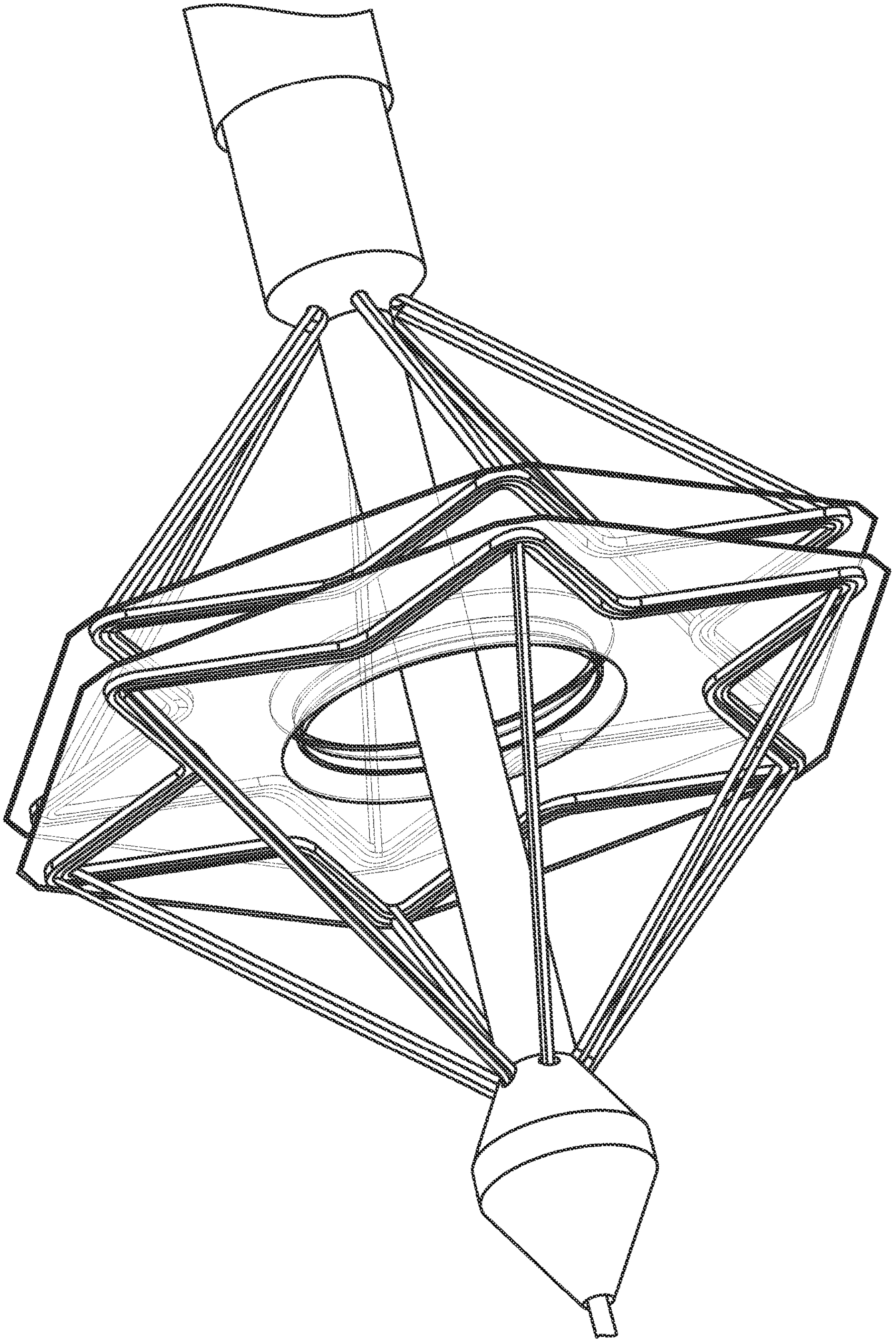
FIG. 21 shows an example implantable medical device for regulating blood pressure and example delivery system in accordance with an embodiment.

FIG. 17 shows an example implantable medical device 1700 for regulating blood pressure and example delivery system 1750 in accordance with an embodiment. As discussed in detail above, the medical device 1700 includes a first frame component 1702, a second frame component 1704, and a conduit portion 130. The medical device 1700 also includes a membrane 132 coupled to the frame components 1702, 1704 and forming the conduit portion 130 as discussed in detail above.

Figure 22:
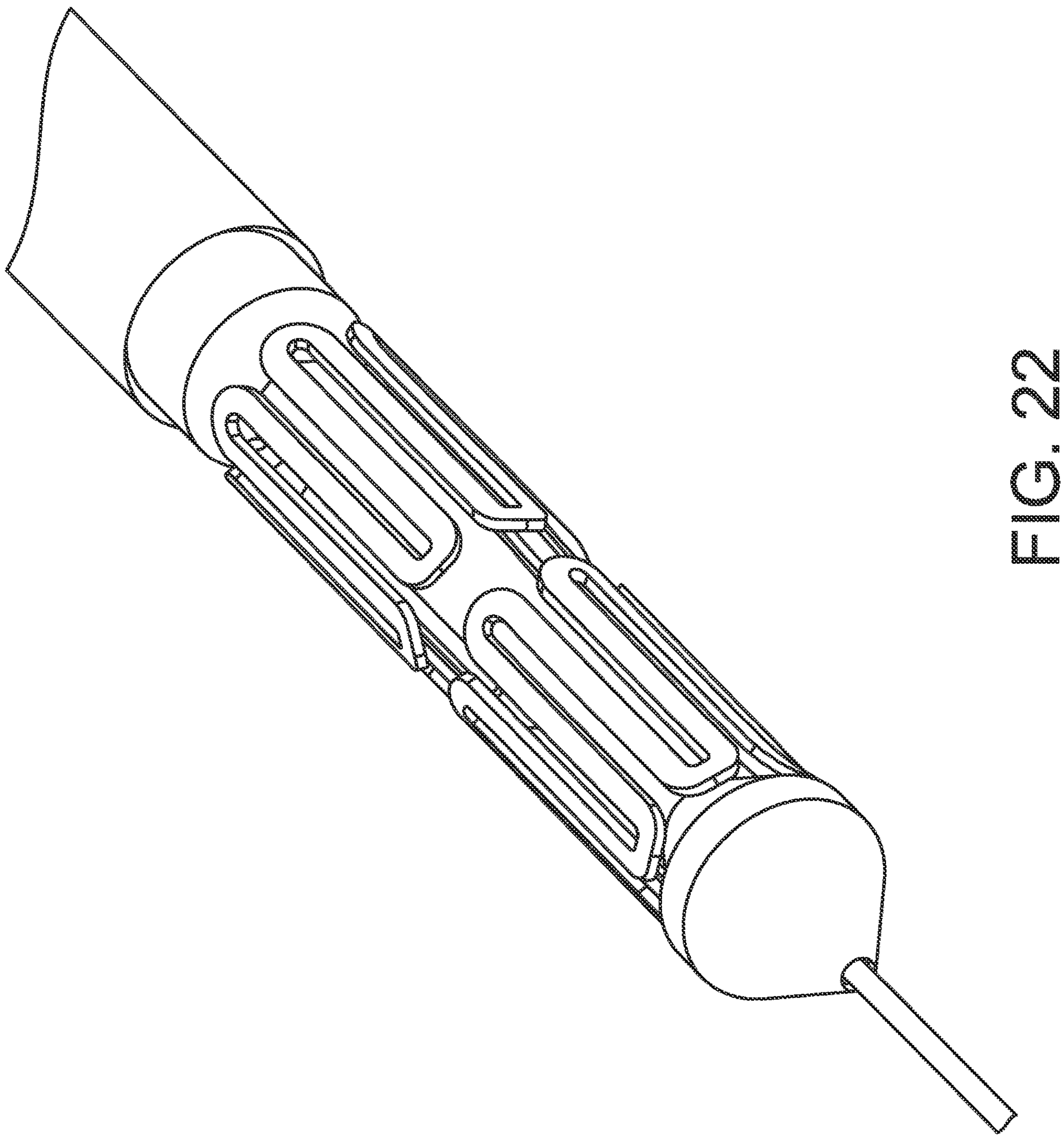
FIG. 22 shows an example implantable medical device for regulating blood pressure in a delivery configuration and example delivery system in accordance with an embodiment.

The delivery system 1750 may include a delivery sheath 1752 that is configured to contain the medical device 1700 in a collapsed or delivery configuration. The delivery system 1750 may also include an inner catheter 1754 and tethers 1756 that engage a portion of one or both of the frame components 1702, 1704 (e.g., by way of eyelets as discussed above). The tethers 1756 may collapse the frame components 1702, 1704 toward the inner catheter 1754 in response to tension. The medical device 1700 may collapsed to a delivery configuration (as shown, for example, in FIG. 22). FIGS. 18-21 shows other example implantable medical devices for regulating blood pressure and with delivery systems and FIG. 22 shows a collapsed configuration of the devices.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An implantable medical device, comprising:
a first frame component configured to conform to an anatomy of a patient;
a second frame component configured to conform to an anatomy of a patient wherein at least one of the first frame component and the second frame component includes inner apices and outer apices, and one or more eyelets arranged with at least one of the outer apices and the inner apices; and
wherein at least one of the first frame component and the second frame component includes a star shape having the inner apices and the outer apices and the one or more eyelets includes a plurality of eyelets pairs with one of the plurality of eyelet pairs arranged on an exterior side of one of the first frame component and the second frame component at the inner apices and one of the plurality of eyelet pairs arranged on an interior side of one of the first frame component and the second frame component at the outer apices.

2. The implantable medical device of claim 1, wherein the plurality of eyelets pairs include a first plurality of eyelet pairs each arranged adjacent the inner apices and a second plurality of eyelet pairs each arranged adjacent the outer apices.

3. The implantable medical device of claim 1, wherein at least one of the first frame component and the second frame includes a first surface and a second surface, and the plurality of eyelet pairs extend about the frame element along one or both of the first surface and the second surface.

4. The implantable medical device of claim 3, wherein the plurality of eyelet pairs extend about the frame element and are arranged alternatively on the first surface and the second surface.

5. The implantable medical device of claim 1, wherein at least one of the inner apices and the outer apices include one or more greater width portions and one or more lesser width portions arranged between the at least one of the inner apices and the outer apices.

6. The implantable medical device of claim 5, wherein at least one of the first frame component and the second frame component includes two greater width portions and one lesser width portion in between two apices of the apices.

7. The implantable medical device of claim 6, wherein the plurality of eyelet pairs are arranged with the one or more greater width portions.

8. The implantable medical device of claim 1, further including one or more tethers coupled to the first frame component and the second frame component and arranged through the conduit portion.

9. The implantable medical device of claim 1, further including a membrane includes a first layer and a second layer that sandwich the first frame component and the second frame component.

10. The implantable medical device of claim 9, wherein the one or more tethers are configured to structurally enhance the conduit portion.

11. An implantable medical device, comprising:

a first frame component configured to conform to an anatomy of a patient;

a second frame component configured to conform to an anatomy of a patient wherein at least one of the first frame component and the second frame component includes inner apices and outer apices, and one or more eyelets arranged on an interior side of the outer apices and on the exterior side of the inner apices.

12. The implantable medical device of claim 11, further including a conduit portion arranged between the first frame component and the second frame component and one or more tethers coupled to the first frame component and the second frame component and arranged through the conduit portion.

13. The implantable medical device of claim 12, wherein the one or more tethers are configured to structurally enhance the conduit portion.

14. An implantable medical device, comprising:

a first frame component configured to conform to an anatomy of a patient;

a second frame component configured to conform to an anatomy of a patient wherein at least one of the first frame component and the second frame component includes inner apices and outer apices, and one or more eyelets arranged with at least one of the outer apices and the inner apices; and wherein at least one of the first frame component and the second frame component includes a star shape having the inner apices and the outer apices and the one or more eyelets includes a plurality of eyelets pairs with one of the plurality of eyelet pairs arranged on an interior side of one of the first frame component and the second frame component and one of the plurality of eyelet pairs arranged on an exterior side of one of the first frame component and the second frame component, wherein the implantable medical device further comprises a conduit portion arranged between the first frame component and the second frame component, the conduit portion including a membrane connecting the first frame component and the second frame component, the conduit portion defining a lumen and the first and second frame components configured to laterally force the conduit portion open in a deployed configuration.

* * * * *